(12) United States Patent
Edwards

(10) Patent No.: US 11,771,862 B2
(45) Date of Patent: Oct. 3, 2023

(54) PATIENT INTERFACE

(71) Applicant: RESMED PTY LTD, Bella Vista (AU)

(72) Inventor: Craig David Edwards, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/641,317

(22) PCT Filed: Sep. 8, 2020

(86) PCT No.: PCT/AU2020/050944
§ 371 (c)(1),
(2) Date: Mar. 8, 2022

(87) PCT Pub. No.: WO2021/046593
PCT Pub. Date: Mar. 18, 2021

(65) Prior Publication Data
US 2022/0347417 A1    Nov. 3, 2022

Related U.S. Application Data

(60) Provisional application No. 62/961,901, filed on Jan. 16, 2020.

(30) Foreign Application Priority Data

Sep. 10, 2019   (AU) ................................ 2019903362

(51) Int. Cl.
*A61M 16/06*        (2006.01)

(52) U.S. Cl.
CPC .... *A61M 16/0666* (2013.01); *A61M 16/0622* (2014.02); *A61M 16/0683* (2013.01)

(58) Field of Classification Search
CPC .......... A61M 16/0069; A61M 16/0072; A61M 16/024; A61M 16/06; A61M 16/0605;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| WO | WO 98/004310 A1 | 2/1998 |
| WO | WO 98/034665 A1 | 8/1998 |

(Continued)

OTHER PUBLICATIONS

International Search Report dated Nov. 23, 2020 issued in International Application No. PCT/2020/050944 (12 pages).

(Continued)

*Primary Examiner* — Annette Dixon
(74) *Attorney, Agent, or Firm* — Nixon & Vanderhye P.C.

(57) ABSTRACT

A patient interface is configured to deliver a pressurized flow of respiratory gas to a patient's airways. The patient interface includes a cradle base configured to cradle the patients nose in use. Two protrusions extend from the cradle base and are configured to be inserted into the patients nares in use. Each of the protrusions have formed therein an opening configured to allow a continuous flow of air therethrough. In addition, a plenum base forms a plenum chamber together with the cradle base. The cradle base is configured so that movement of the cradle base is decoupled from the plenum base.

45 Claims, 28 Drawing Sheets

(58) Field of Classification Search
CPC .......... A61M 16/0611; A61M 16/0616; A61M 16/0622; A61M 16/0633; A61M 16/0644; A61M 16/0666; A61M 16/0672; A61M 16/0683; A61M 16/08; A61M 16/0816; A61M 16/0825; A61M 16/0833; A61M 16/085; A61M 16/0866; A61M 16/0875; A61M 16/10; A61M 16/105; A61M 16/1055; A61M 16/107; A61M 16/109; A61M 16/1095; A61M 16/16; A61M 16/161; A61M 16/20; A61M 16/206; A61M 16/208; A61M 2016/0027; A61M 2016/0039; A61M 2016/0661; A61M 2202/0208; A61M 2202/0225; A61M 2205/0216; A61M 2205/3368; A61M 2205/3653; A61M 2205/42; A61M 2205/502; A61M 2205/7518; A61M 2207/00; A61M 2210/0618; A62B 9/04

See application file for complete search history.

(56) References Cited

U.S. PATENT DOCUMENTS

| | | | |
|---|---|---|---|
| 5,074,297 A * | 12/1991 | Venegas | A61M 16/0611 |
| | | | 128/205.13 |
| 5,687,715 A | 11/1997 | Landis | |
| 5,724,965 A | 3/1998 | Handke et al. | |
| 6,431,172 B1 * | 8/2002 | Bordewick | A61M 16/0666 |
| | | | 128/207.18 |
| 6,532,959 B1 | 3/2003 | Berthon-Jones | |
| 6,581,594 B1 | 6/2003 | Drew et al. | |
| 7,448,386 B2 | 11/2008 | Ho et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,985,115 B2 * | 3/2015 | Baecke | A61M 16/0616 |
| | | | 128/207.13 |
| 9,010,330 B2 | 4/2015 | Barlow et al. | |
| 9,095,673 B2 | 8/2015 | Barlow et al. | |
| 10,543,332 B2 | 1/2020 | Scheiner et al. | |
| 11,179,534 B2 | 11/2021 | Henry et al. | |
| 2003/0172936 A1 * | 9/2003 | Wilkie | A61M 16/0683 |
| | | | 128/207.18 |
| 2007/0144525 A1 | 6/2007 | Davidson et al. | |
| 2009/0000623 A1 * | 1/2009 | Lynch | A61M 16/0622 |
| | | | 128/206.24 |
| 2009/0044808 A1 | 2/2009 | Guney et al. | |
| 2009/0050156 A1 | 2/2009 | Ng et al. | |
| 2009/0095298 A1 | 4/2009 | Gunaratnam et al. | |
| 2009/0095301 A1 * | 4/2009 | Hitchcock | A61M 16/0683 |
| | | | 128/206.21 |
| 2010/0000534 A1 | 1/2010 | Kooij et al. | |
| 2011/0146685 A1 | 6/2011 | Allan et al. | |
| 2014/0261432 A1 | 9/2014 | Eves et al. | |
| 2016/0095996 A1 * | 4/2016 | Gusky | A61M 16/0816 |
| | | | 128/205.25 |
| 2016/0361510 A1 * | 12/2016 | Alphonse | A61M 16/06 |
| 2019/0125996 A1 | 5/2019 | Bentley et al. | |
| 2020/0054850 A1 | 2/2020 | Davidson | |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | 2010/131189 | 11/2010 |
| WO | WO 2010/135785 A1 | 12/2010 |
| WO | WO 2012/171072 A1 | 12/2012 |
| WO | WO 2013/020167 A1 | 2/2013 |

OTHER PUBLICATIONS

Written Opinion of the International Searching Authority dated Nov. 23, 2020 issued in International Application No. PCT/2020/050944 (14 pages).
Written Opinion of the International Searching Authority dated Jul. 26, 2021 issued in International Application No. PCT/2020/050944 (8 pages).
Written Opinion of the International Searching Authority dated Oct. 15, 2021 issued in International Application No. PCT/2020/050944 (4 pages).
International Preliminary Report on Patentability dated Dec. 23, 2021 issued in International Application No. PCT/2020/050944 (28 pages).
"*Respiratory Physiology*", by John B. West, Lippincott Williams & Wilkins, 9$^{th}$ edition published 2012 (8 pages).

* cited by examiner

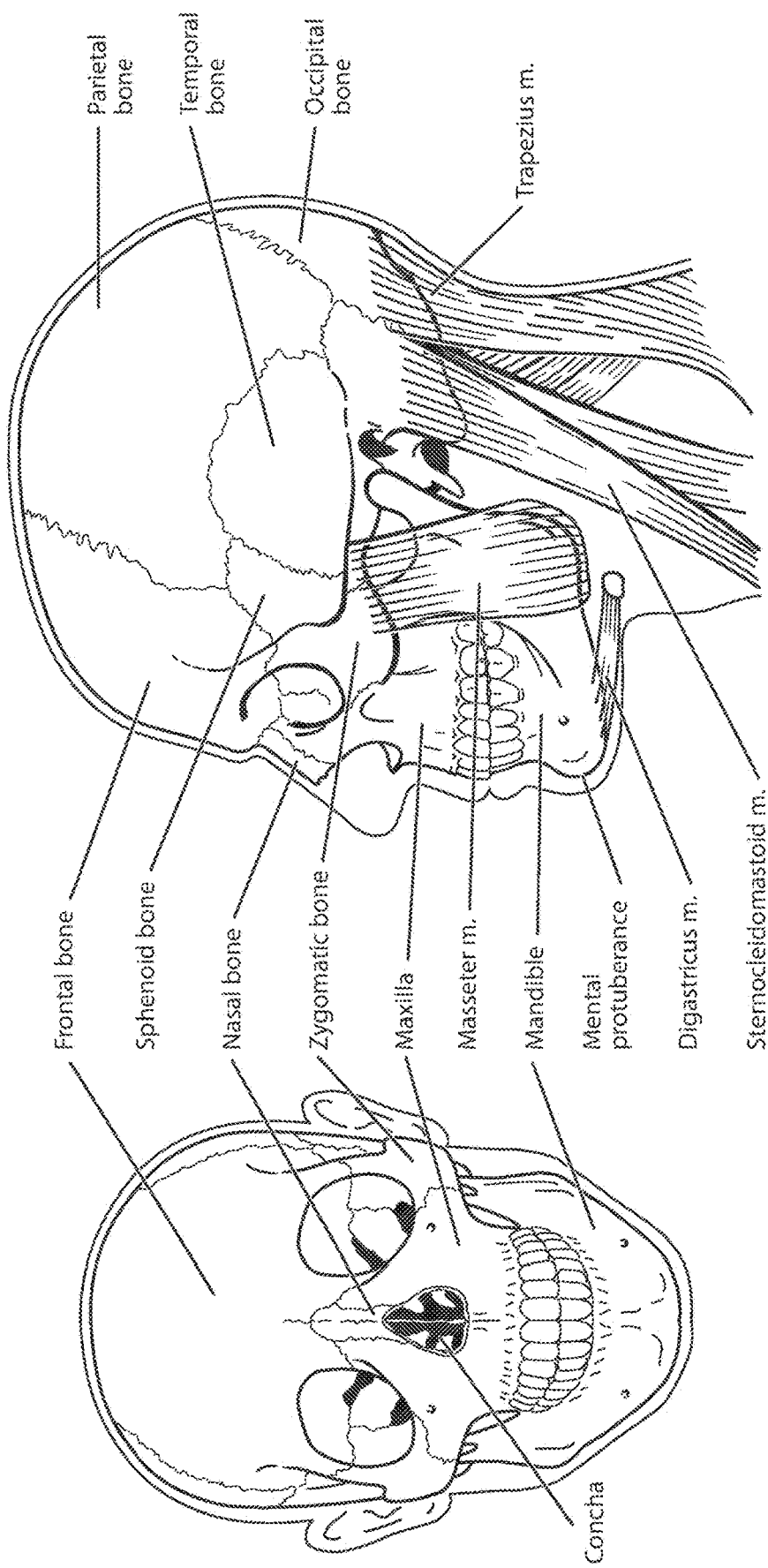

Relatively Large Positive Curvature

Relatively Small Positive Curvature

Zero Curvature

Relatively Small Negative Curvature

Relatively Large Negative Curvature

FIG. 3O Left-hand rule

FIG. 3P Right-hand rule

FIG. 3Q Left ear helix

FIG. 3S Right-hand helix Right-hand positive

FIG. 3R Right ear helix

PATIENT INTERFACE

1 CROSS-REFERENCE TO RELATED APPLICATIONS

This application is the U.S. national phase of International Application No. PCT/AU2020/050944 filed Sep. 8, 2020 which designated the U.S. and claims priority to AU 2019903362 filed Sep. 10, 2019, and claims priority to U.S. provisional Application No. 62/961,901 filed Jan. 16, 2020, the entire contents of each of which are hereby incorporated by reference.

This application claims the benefit of Australian Application No. 2019903362, filed Sep. 10, 2019 and U.S. Provisional Application No. 62/961,901, filed on 16 Jan. 2020, which is incorporated by reference in its entirety.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

An alternative type of treatment system comprises a patient interface in which a tube or substantially hollow elongate structure that delivers pressurised air to the patient's airways also functions as part of the structure that positions and stabilises the seal-forming portion of the patient interface to the appropriate part of the patient's face, e.g. the headgear. This means that the headgear forms part of the air circuit. For the purposes of this specification the terms "tube" and "conduit" should be considered to have the same meaning, unless the context clearly indicates otherwise.

This type of patient interface may be referred to as incorporating 'headgear tubing' or 'conduit headgear', these terms being understood to be interchangeable for the purposes of this specification unless the context indicates otherwise. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. 2007/0246043, the contents of which are incorporated herein by reference, in which the conduit connects to the patient interface through a port positioned in use on top of the patient's head.

The Philips DreamWear™ mask includes such conduit headgear/headgear tubing. The length of the DreamWear™ headgear tubes cannot be adjusted. Consequently, the DreamWear™ headgear is supplied in three different sizes to cater for different sized patient faces. Providing a greater number of different sizes may increase the complexity and cost to manufacture the headgear and may result in larger packaging. Additionally, a supply of discretely sized masks may limit the extent to which differently sized patient heads can be accommodated. There may be a greater chance of some patients being unable to achieve what they consider a comfortable fit if forced to choose between discrete sizes that are not adjustable in length.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/34,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH$_2$O Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology is directed to a patient interface that includes a plenum structure, a seal forming structure, and a position and stabilizing structure configured to support the seal forming structure and the plenum structure on the patient's head. The patient interface may include a vent system.

Another aspect of the present technology is directed to a patient interface configured to deliver a pressurized flow of respiratory gas to a patient's airways. The patient interface may include a cradle base configured to cradle the patient's nose in use and two protrusions extending from the cradle base and being configured to be inserted into the patient's nares in use.

Another aspect of the present technology is directed to a seal-forming structure for a patient interface that is configured to form a seal with the patient's nares. The seal-forming structure may comprise a base portion and two protrusions provided to the base portion, each of the protrusions having formed therein an opening configured to allow a continuous flow of air therethrough. In example forms of the technology the protrusions are structured and arranged to be inserted into, or partly into, a respective one of the patient's nares in use. The protrusions may be structured and arranged to seal, in use, with an inner peripheral edge of the respective naris. The protrusions may comprise ends that, in use, seal with an inner peripheral edge of the respective naris.

In examples, the base portion further comprises lateral extension portions extending laterally outwards on either side of the two protrusions, the lateral extension portions respectively being configured to seal against a lateral or inferior part of each of the patient's nasal ala in use.

In examples, the base portion is formed such that, in the absence of any forces acting on the base portion, the base portion has a positive curvature in a lateral direction and wherein, when donned by the patient, engagement of the base portion with the nose decreases the positive curvature of the base portion.

An aspect of the present technology is directed to a seal-forming structure for a patient interface that is configured to form a seal with the patient's nares. The seal-forming structure may comprise a base portion and at least one opening in the base portion configured to allow a continuous flow of air therethrough. In example forms of the technology the base portion is provided to a plenum chamber. A part of the base portion and/or a part of the plenum chamber may form one or more folds. In examples, the seal-forming structure comprises two protrusions provided to the base portion, each of the protrusions having formed therein one of the openings.

An aspect of the present technology is directed to a patient interface that comprises: a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, the seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to ambient, said vent structure being sized and shaped to maintain the therapeutic pressure in the plenum chamber in use, wherein the seal-forming structure further comprises a base portion and two protrusions provided to the base portion, each of the protrusions having formed therein an opening configured to allow a continuous flow of air therethrough, the protrusions being structured and arranged to be inserted into, or partly into, a respective one of the patient's nares in use to provide the flow of air at said therapeutic pressure to the patient's nares.

An aspect of the present technology is directed to a patient interface that comprises: a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, the seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to ambient, said vent structure being sized and shaped to maintain the therapeutic pressure in the plenum chamber in use, wherein the seal-forming structure comprises a base portion and at least one opening in the base portion configured to provide the flow of air at said therapeutic pressure to the patient's nares in use, wherein the base portion is provided to a plenum chamber and a part of the base portion and/or a part of the plenum chamber form(s) one or more folds. In examples, the seal-forming structure comprises two protrusions provided to the base portion, each of the protrusions having formed therein one of the openings.

In examples, the base portion further comprises lateral extension portions extending laterally outwards on either side of the two protrusions, the lateral extension portions being configured to seal respectively against a lateral or inferior part of each of the patient's nasal ala in use.

In examples, the base portion is formed such that, in the absence of any forces acting on the base portion, the base portion has a positive curvature and wherein, when donned by the patient, engagement of the base portion with the nose decreases the positive curvature of the base portion.

In examples, the patient interface further comprises a positioning and stabilising structure to provide a force to hold the seal-forming structure in a therapeutically effective position on the patient's head. In one example the positioning and stabilising structure comprises a tie, the tie being constructed and arranged so that at least a portion overlies a region of the patient's head superior to an otobasion superior of the patient's head in use. In another example the positioning and stabilising structure comprises at least one gas delivery tube constructed and arranged to contact at least a region of the patient's head superior to an otobasion superior of the patient's head in use, wherein a portion of the gas delivery tube superior to the otobasion superior of the patient's head comprises, or is provided to, a connection port configured to receive the flow of air from the air circuit and to deliver the flow of air to the entrance of the patient's airways via the seal-forming structure.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Another aspect of the technology includes a patient interface configured to deliver a pressurized flow of respiratory gas to a patient's airways. The patient interface may include a cradle base configured to cradle the patient's nose in use. Two protrusions may extend from the cradle base and may be configured to be inserted into the patient's nares in use. Each of the protrusions may have formed therein an opening configured to allow a continuous flow of air therethrough. A plenum base may, together with the cradle base, form a plenum chamber. The cradle base may be configured so that movement of the cradle base is decoupled from the plenum base.

The protrusions may be structured and arranged to seal, in use, with an inner peripheral edge of the respective naris. In addition, the protrusions may comprise ends that, in use, seal with an inner peripheral edge of the respective naris.

The cradle base may include lateral extension portions extending laterally outwards on either side of the two protrusions. The lateral extension portions may respectively be configured to seal against a lateral or inferior part of each of the patient's nasal ala in use. In addition, the cradle base may be configured to be outwardly flexed by the patient's nose when donned by the patient.

The protrusions may have a frusto-conical shape. In addition, the openings of the protrusions may be angled relative to the portions of the cradle base surface from which the protrusions extend.

The plenum base may include a pair of air inlets on opposing lateral sides. In addition, the plenum base and the cradle base may be inflatable.

A buffer or damper between the cradle base and the plenum base may be configured to decouple movement of the cradle base from the plenum base. The buffer or damper may not be configured to decouple movement between two sealing surfaces. Also, the buffer or damper may not be configured to decouple movement between a nasal seal and a mouth seal. The patient interface may not comprise a mouth seal. Also, the protrusions may not include stalks.

Another aspect of the technology includes a patient interface configured to deliver a pressurized flow of respiratory gas to a patient's airways. The patient interface may include a plenum base and a cradle base attached to the plenum base. The plenum base may be configured to cradle the patient's nose in use. The plenum base and the cradle base may together form a plenum chamber. A channel in a surface of the plenum base adjacent to the cradle base may be configured to decouple movement of the cradle base from the plenum base. In addition, a pair of projections may extend from the cradle base. The pair of projections may be configured to be inserted into the patient's nares in use. The pair of projections may form a gas flow path from the plenum chamber to the patient's airways in use.

The channel may completely surround the cradle base. In addition, the cradle base may be U-shaped or V-shaped. The plenum base and the cradle base may be inflatable. Also, lateral portions of the cradle base may be configured to flex toward and way from plenum base.

Each of the projections may extend from a respective one of the lateral portions of the cradle base. The lateral portions of the cradle base may extend laterally beyond the respective one of the projections.

The plenum base may include a pair of gas inlets. Each gas inlet may be located at a respective lateral side of the plenum base.

Each projection may be configured to seal inside of the patient's nares. At the same time, the cradle base may be configured to seal against an outside surface of patient's nares.

Another aspect of the technology includes a patient interface configured to deliver a pressurized flow of respiratory gas to a patient's airways. The patient interface may include a plenum base pressurisable to a therapeutic pressure of at least 6 cmH$_2$O above ambient air pressure. The plenum base may include a plenum chamber inlet port sized and structured to receive a flow of air at the therapeutic pressure for breathing by the patient. A seal-forming structure may be constructed and arranged to form a seal with a region of the patient's face surrounding and inside the patient's nostrils. The seal-forming structure may also be constructed and arranged to maintain the therapeutic pressure in the plenum chamber throughout the patient's respiratory cycle in use. A spring or damper may be located between the plenum chamber and the seal forming structure. The spring or damper may be configured to decouple movement of the seal-forming structure from the plenum base. The seal-forming structure may further include a cradle base and two protrusions provided to the cradle base. Each of the protrusions may have formed therein an opening configured to allow a continuous flow of air therethrough. The protrusions may be structured and arranged to be inserted into, or partly into, a respective one of the patient's nares in use to provide the flow of air at said therapeutic pressure to the patient's nares.

The protrusions may be configured to form a seal with the inside of the patient's nares. In addition, the cradle base may be configured to cradle the patient's nose and form a seal with a surface outside of the patient's nares, in use.

Only a central portion of cradle base may be attached to plenum base. The lateral portions of the cradle base may be flexible toward and away from plenum base. In addition, the projections may be angled relative to a surface of the cradle base from which the projections extend.

Another aspect of the technology includes a patient interface configured to deliver a pressurized flow of respiratory gas to a patient's airways. The patient interface may include a plenum base pressurisable to a therapeutic pressure of at least 6 cmH$_2$O above ambient air pressure. The plenum base may include an inlet port sized and structured to receive a flow of air at the therapeutic pressure for breathing by the patient. A seal-forming structure may be constructed and arranged to form a seal with a region of the patient's face surrounding and inside the patient's nostrils. The seal-forming structure may also be constructed and arranged to maintain the therapeutic pressure in the plenum base throughout the patient's respiratory cycle in use. The seal-forming structure may include a cradle base and a pair of protrusions extending from the cradle base. Each protrusion may have formed therein an opening configured to convey the flow of air at said therapeutic pressure to the patient's nares in use. Each protrusion may be configured to be inserted into, or partly into, one of the patient's nares in use. The cradle base may be supported on the plenum base and a part of the cradle base and/or a part of the plenum base may form one or more folds configured to decouple movement of the cradle base from the plenum base.

The one or more folds may be part of a concertina structure. In addition, the cradle base may further include lateral extension portions extending laterally outwards on either side of the protrusions. The lateral extension portions may be configured to seal respectively against a lateral or inferior part of each of the patient's nasal ala in use.

The patient interface may further include a positioning and stabilising structure to provide a force to hold the seal-forming structure in a therapeutically effective position on the patient's head. The positioning and stabilising structure may include a tie that is constructed and arranged so that at least a portion overlies a region of the patient's head superior to an otobasion superior of the patient's head in use. The positioning and stabilising structure may also include at least one gas delivery tube constructed and arranged to contact at least a region of the patient's head superior to an otobasion superior of the patient's head in use. A portion of the gas delivery tube superior to the otobasion superior of the patient's head may include or be provided to, a connection port configured to receive the flow of air from the air circuit and to deliver the flow of air to the entrance of the patient's airways via the seal-forming structure.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
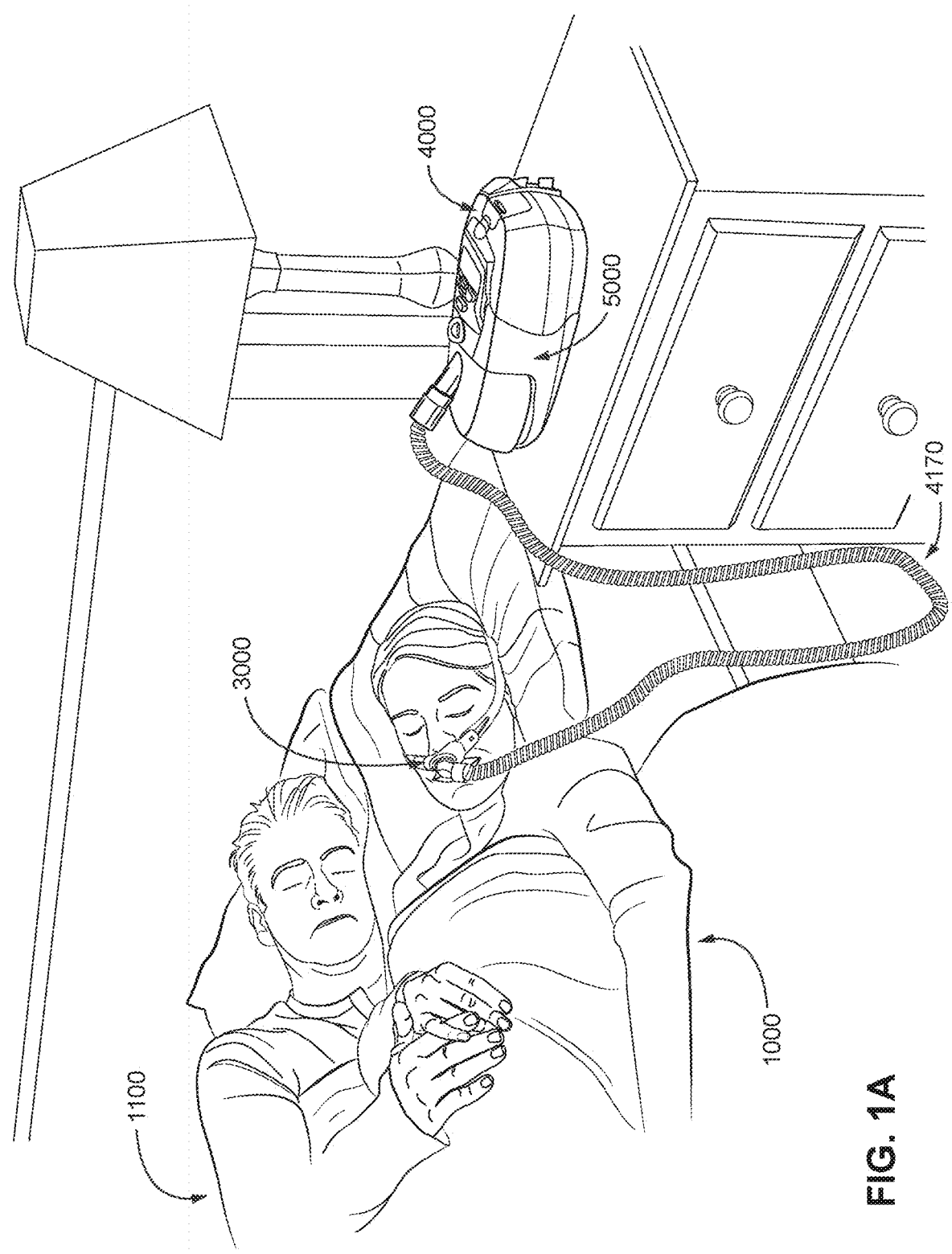
Figure 1B:
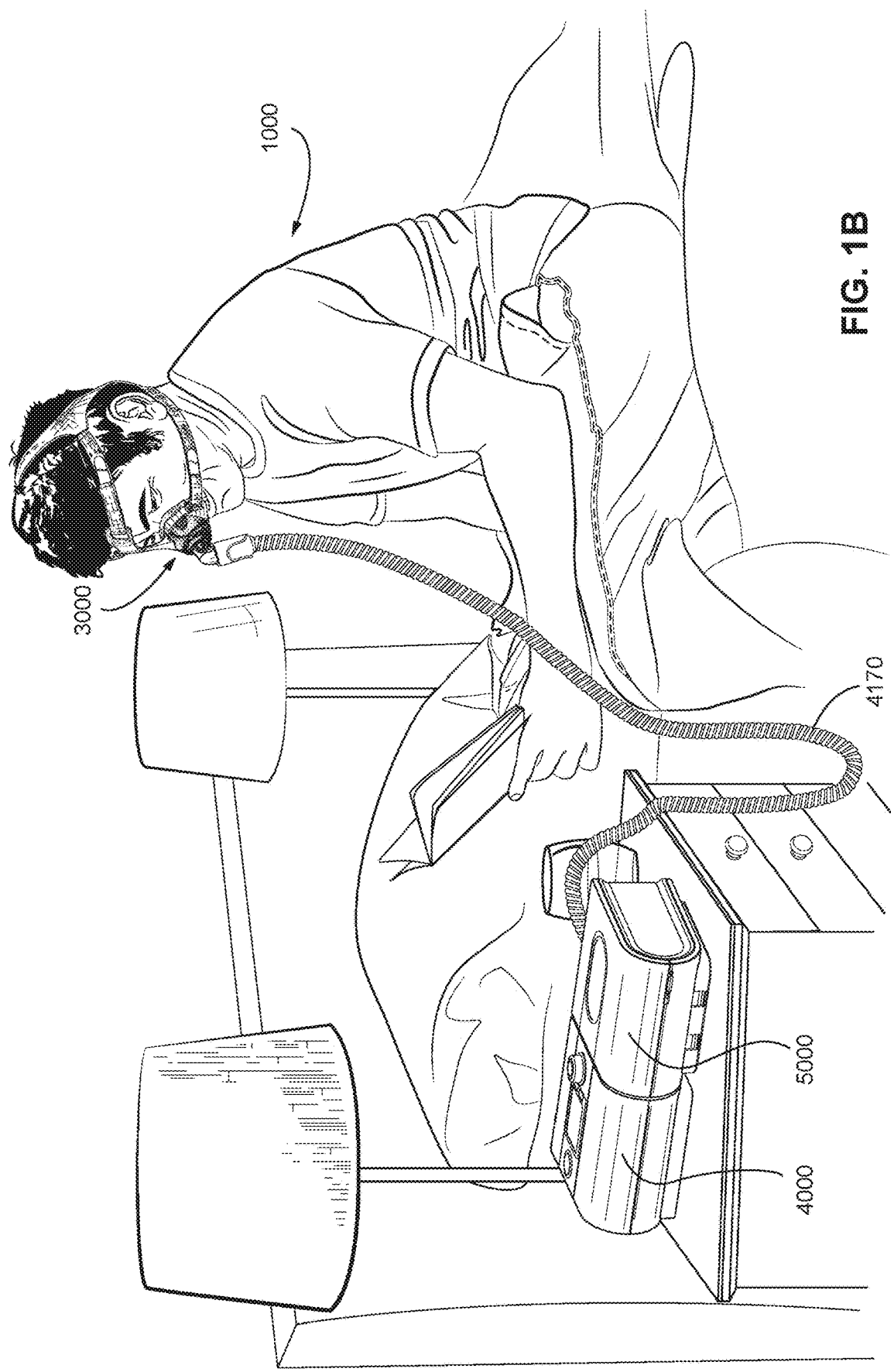
Figure 1C:
Figure 2A:
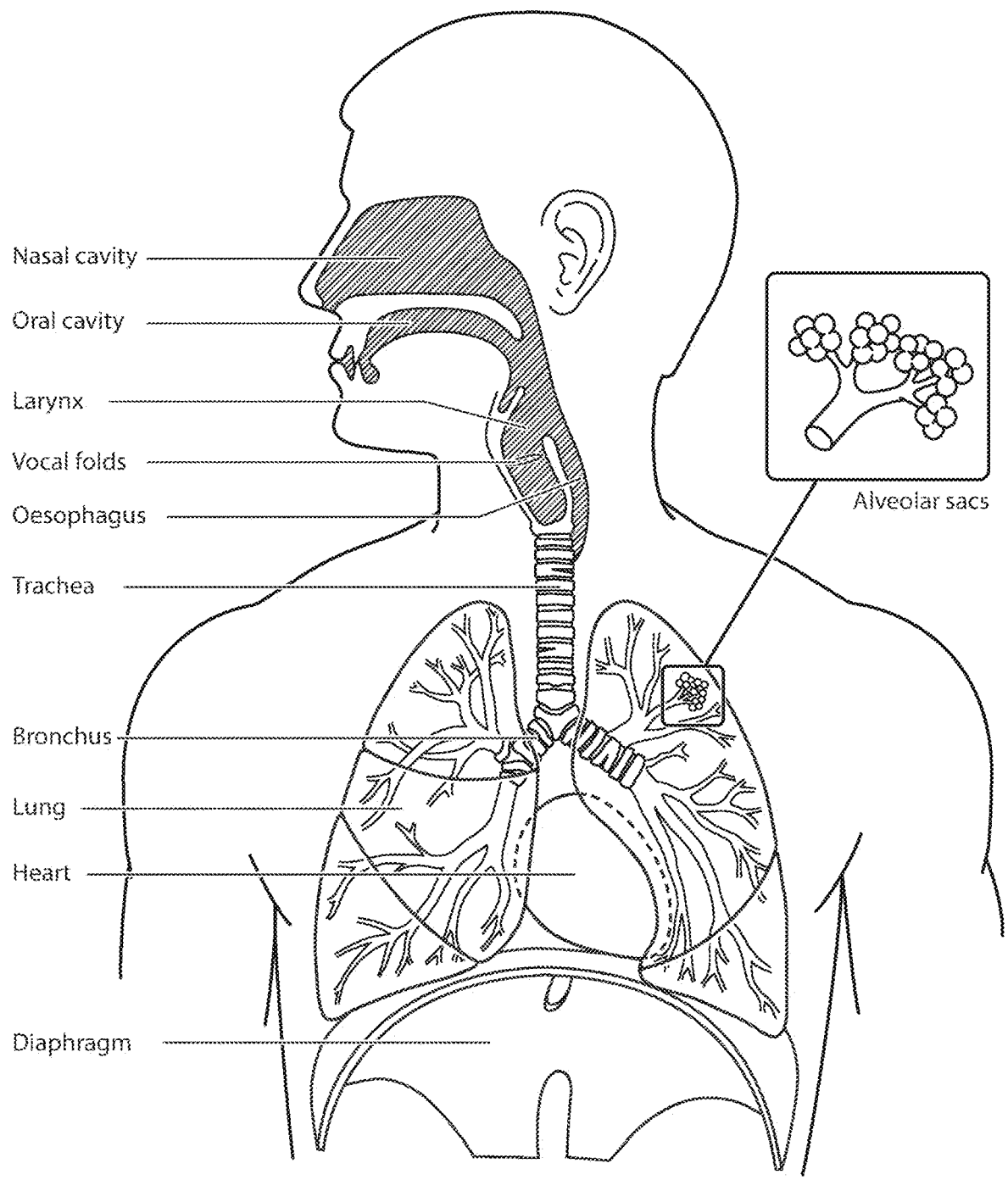
FIG. 2A shows an overview of a human respiratory system including the nasal and oral cavities, the larynx, vocal folds, oesophagus, trachea, bronchus, lung, alveolar sacs, heart and diaphragm.
Figure 2B:
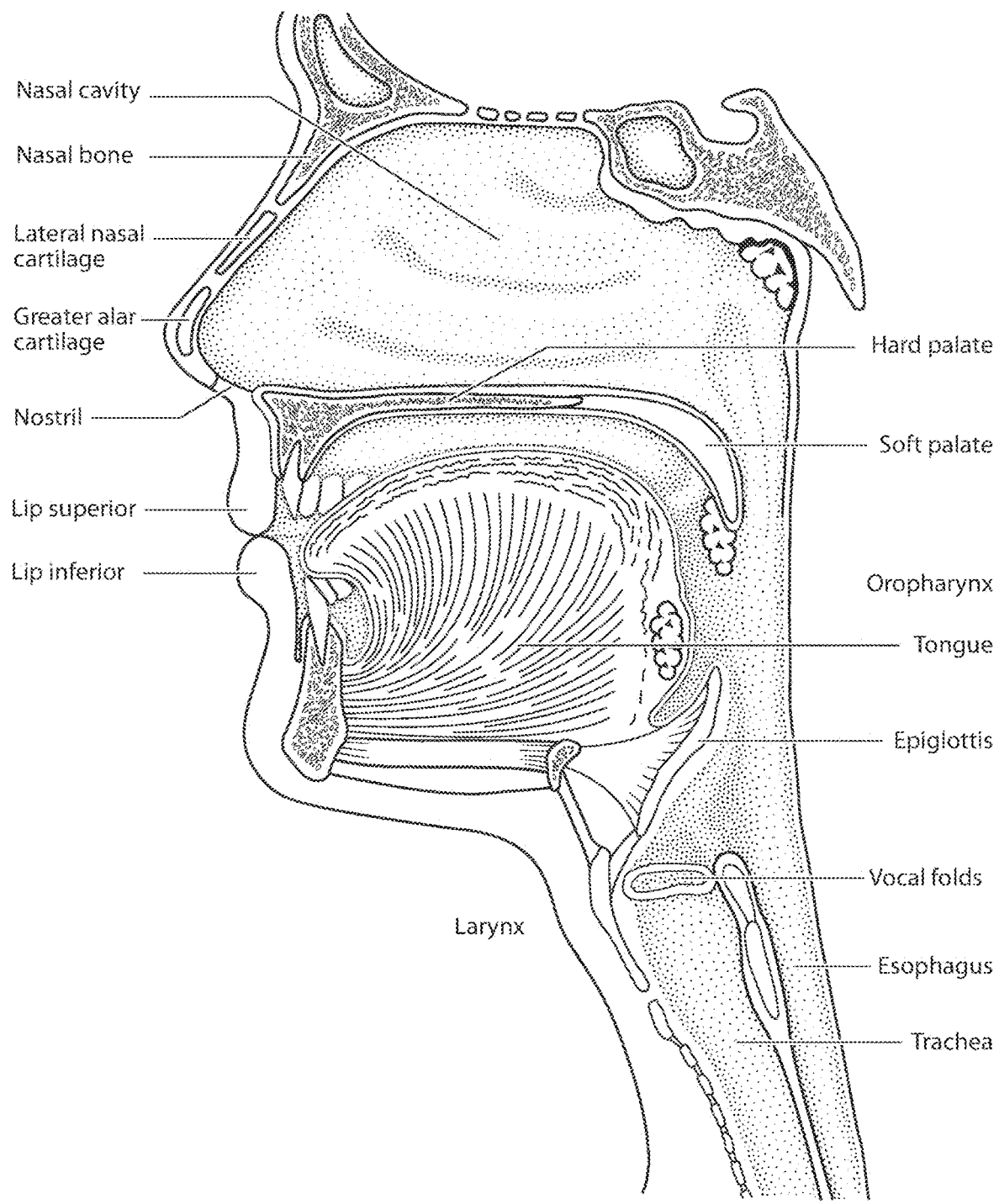
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
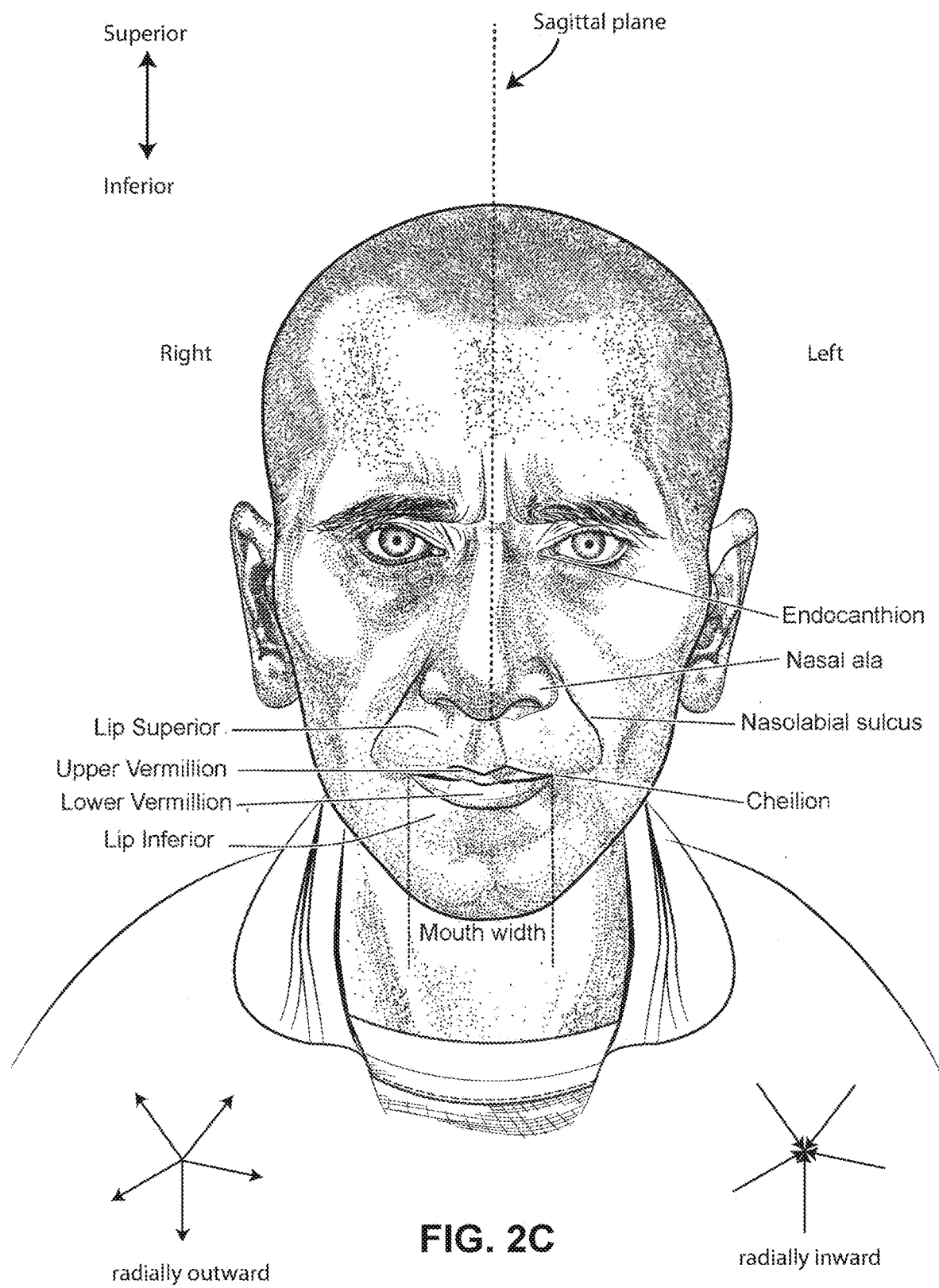
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
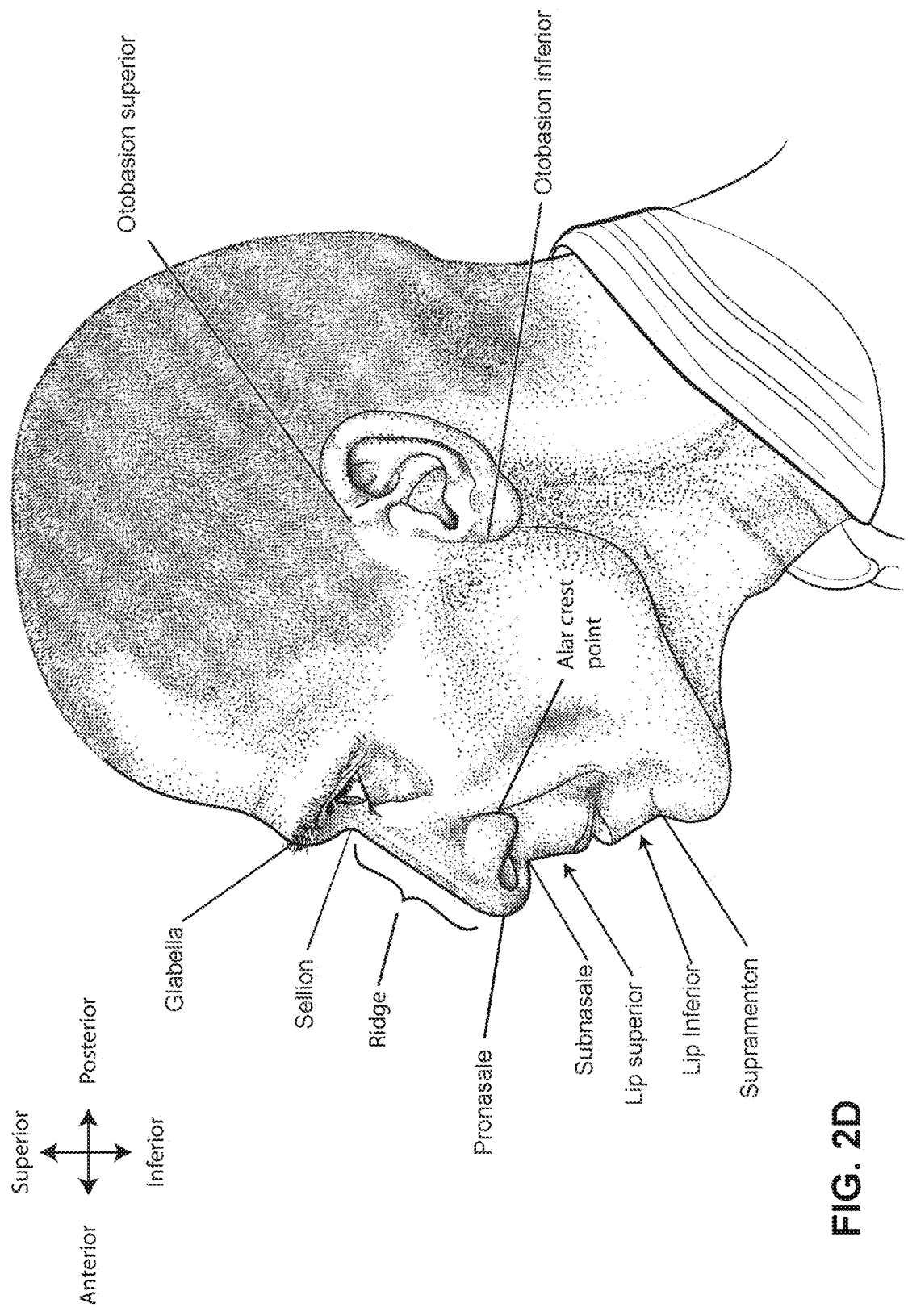
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
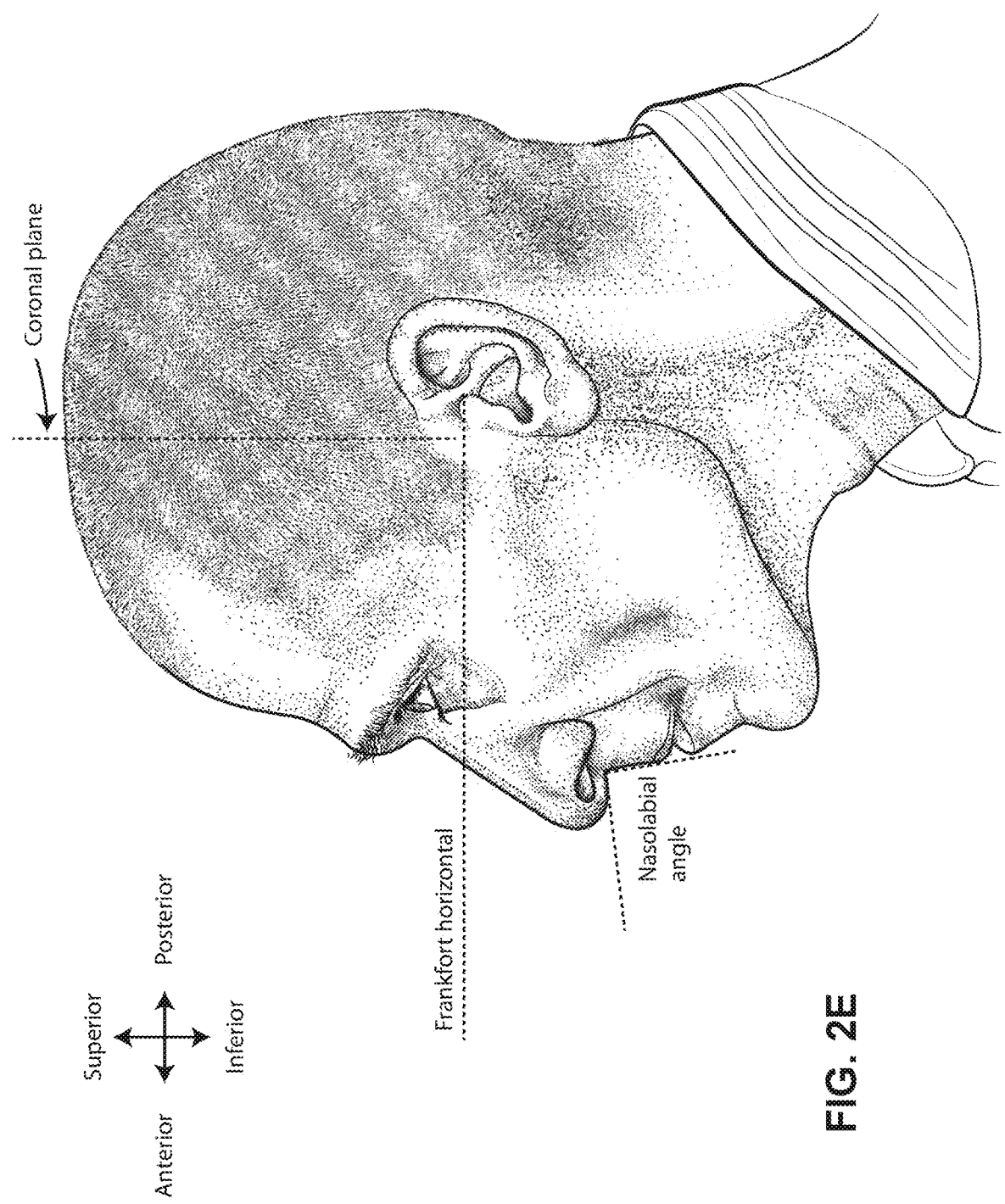

FIG. 2E is a further side view of a head. The approximate locations of the Frankfort horizontal and nasolabial angle are indicated. The coronal plane is also indicated.

Figure 2F:
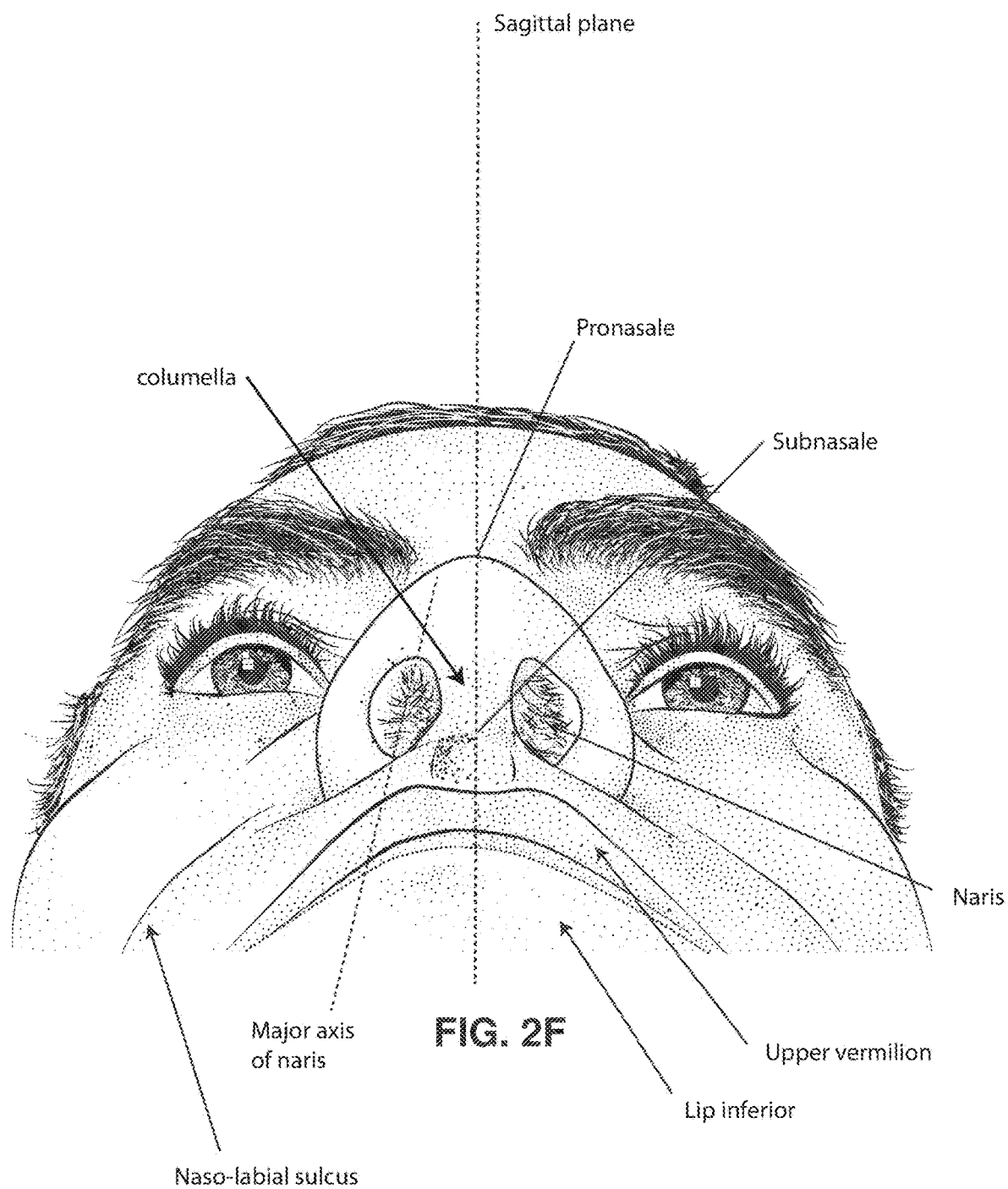

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
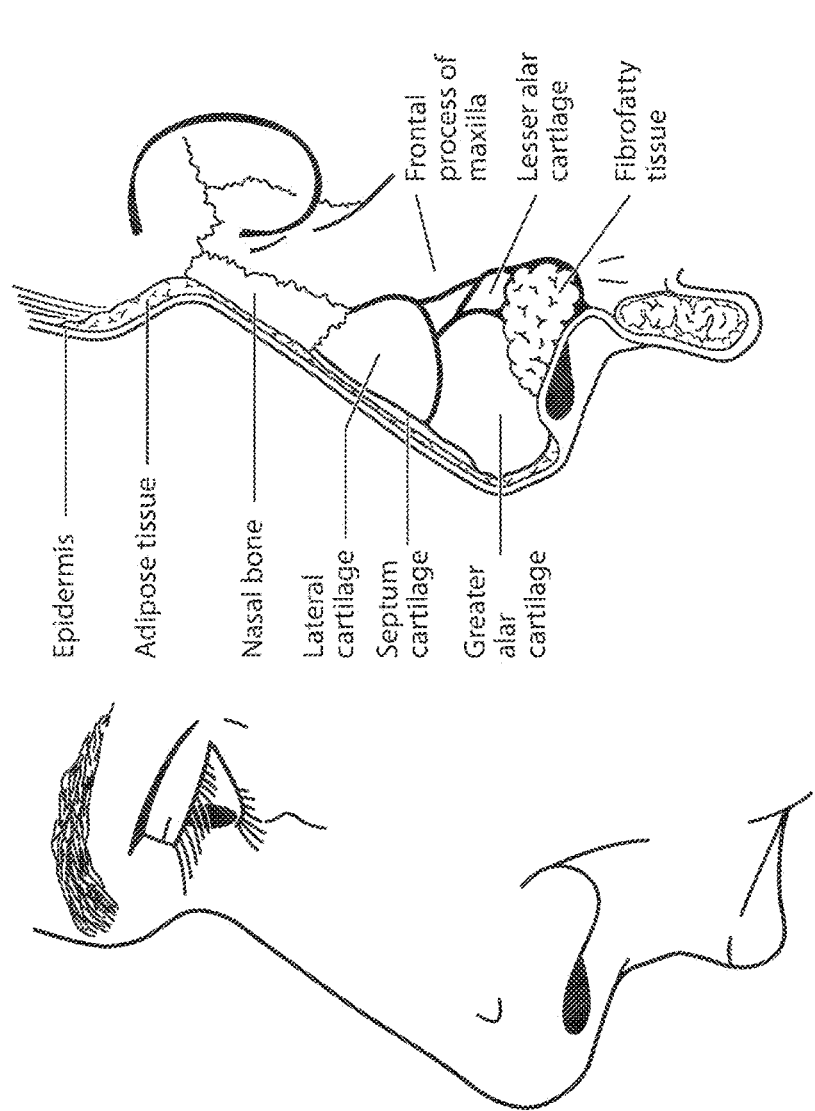

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
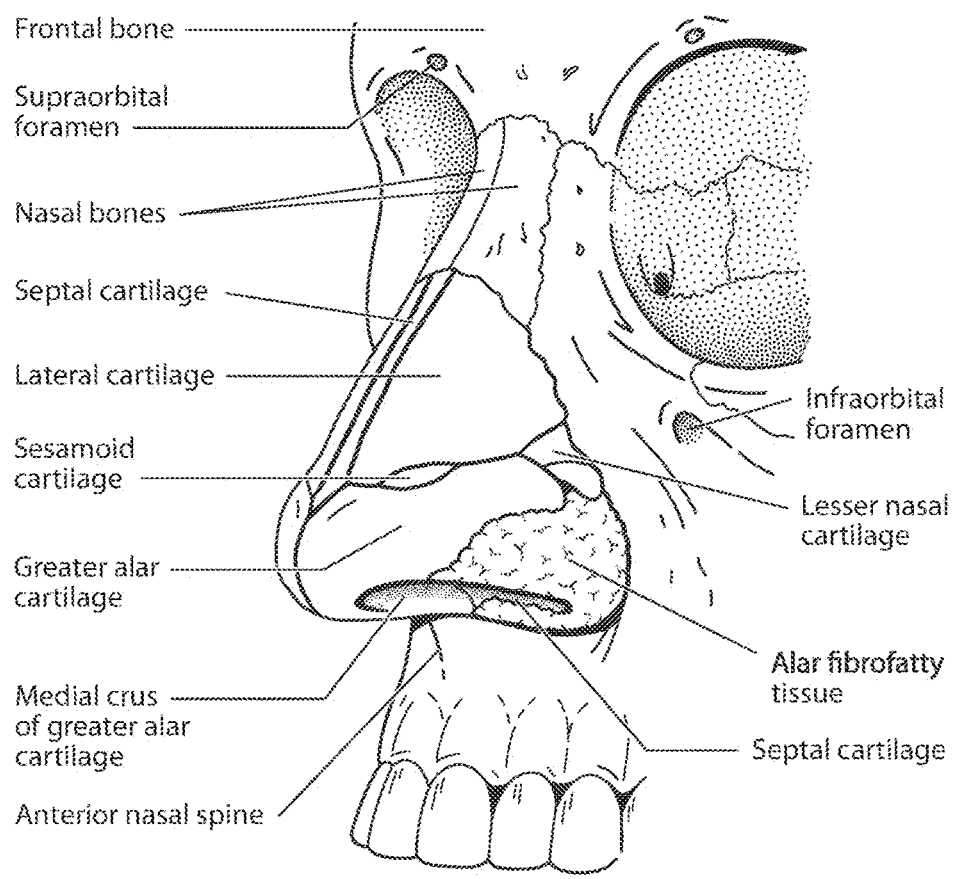

FIG. 2L shows an anterolateral view of a nose.

4.3 Patient Interface

Figure 3A:
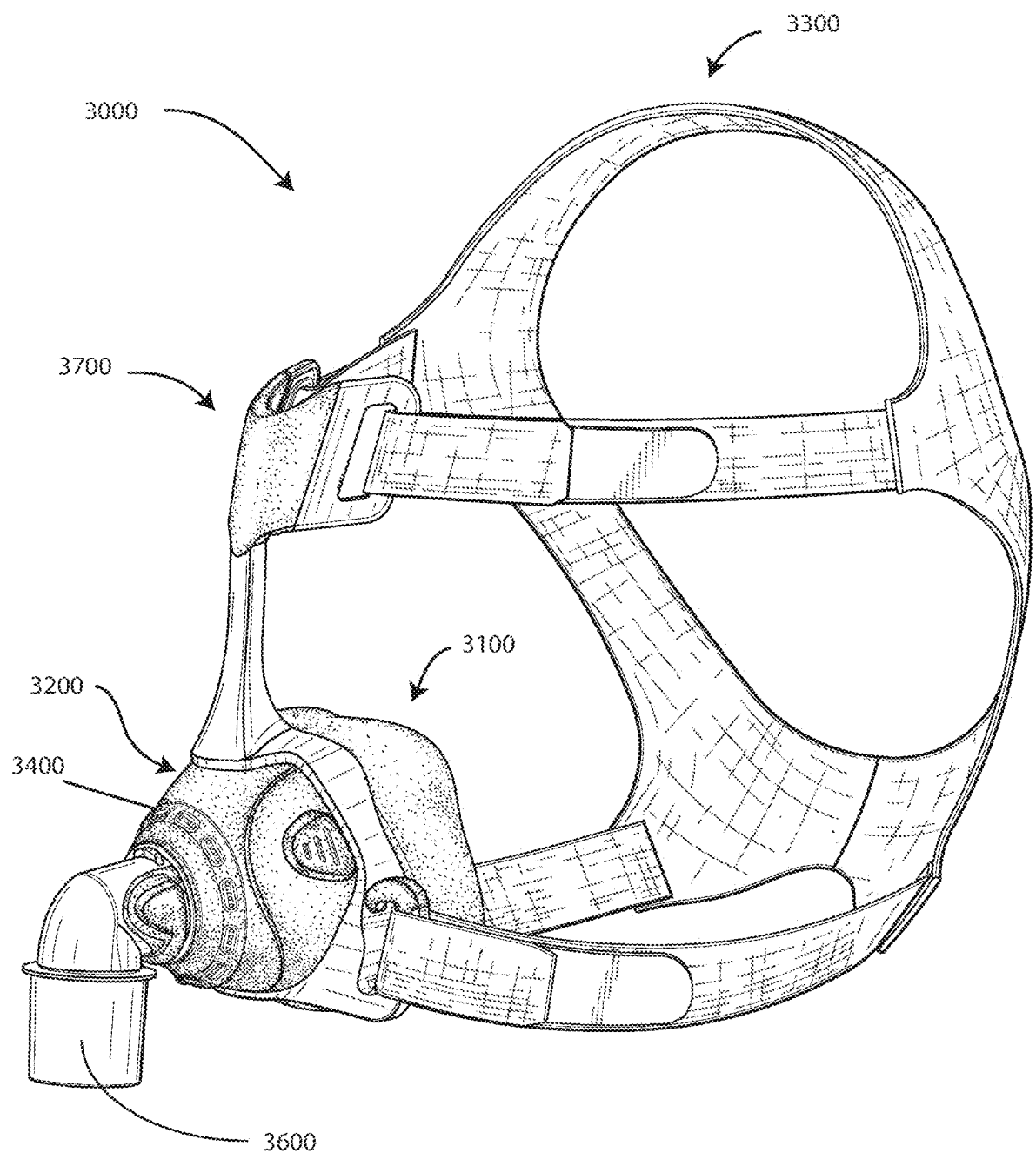

FIG. 3A shows a patient interface in the form of a nasal mask in accordance with one form of the present technology.

Figure 3B:
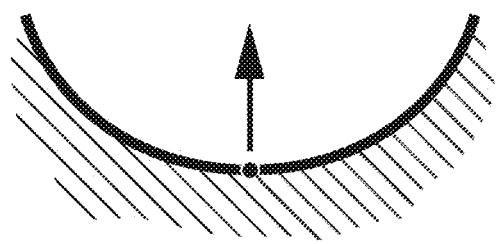

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
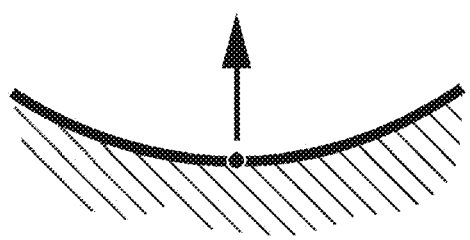

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
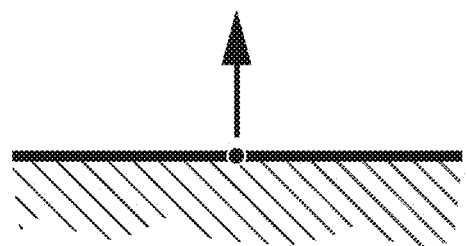

FIG. 3D shows a schematic of a cross-section through a structure at a point. An outward normal at the point is indicated. The curvature at the point has a value of zero.

Figure 3E:
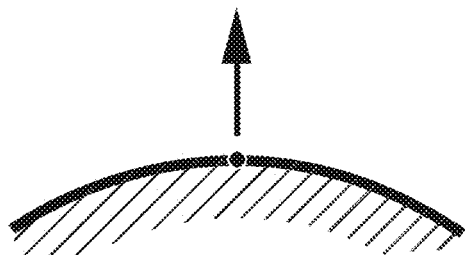

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
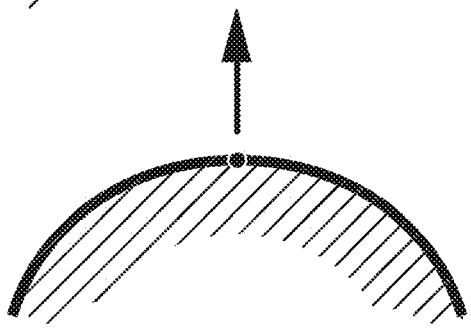

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
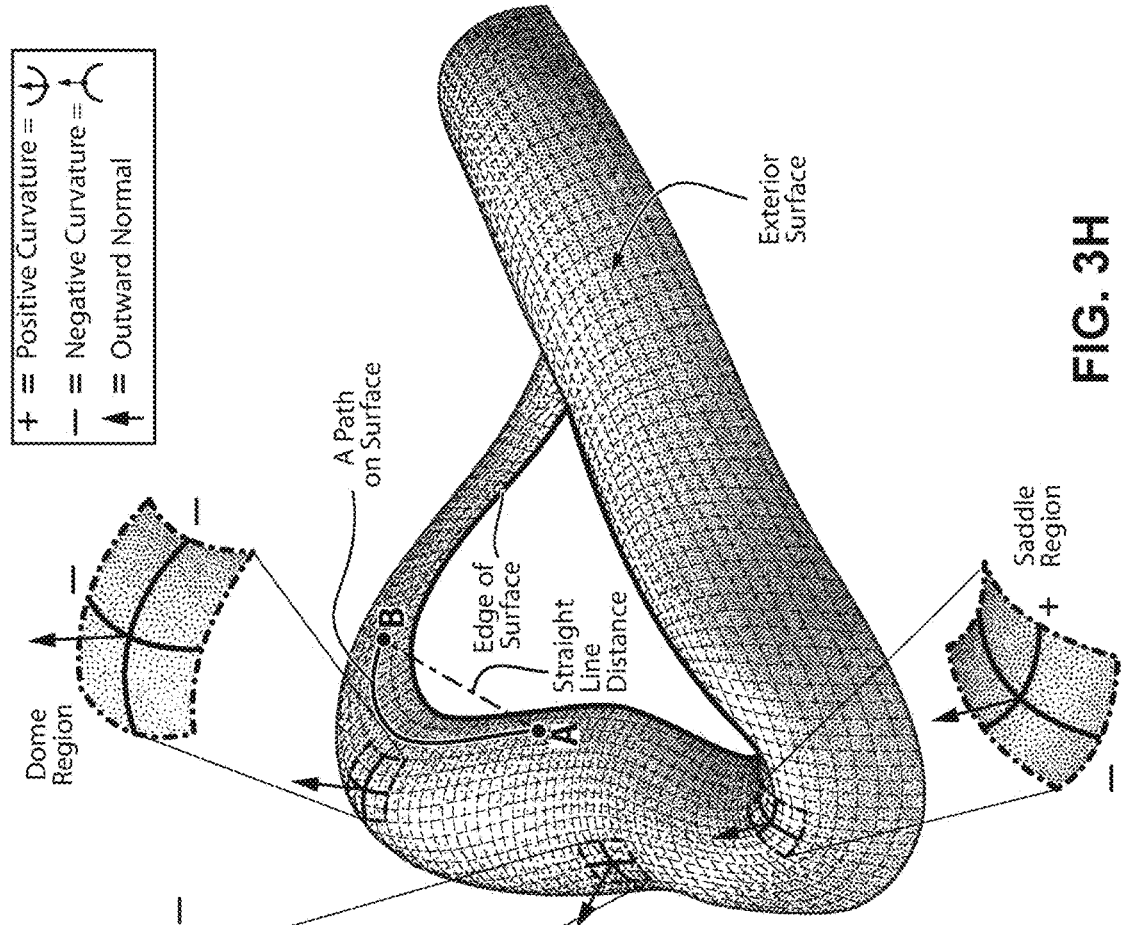
Figure 3G:
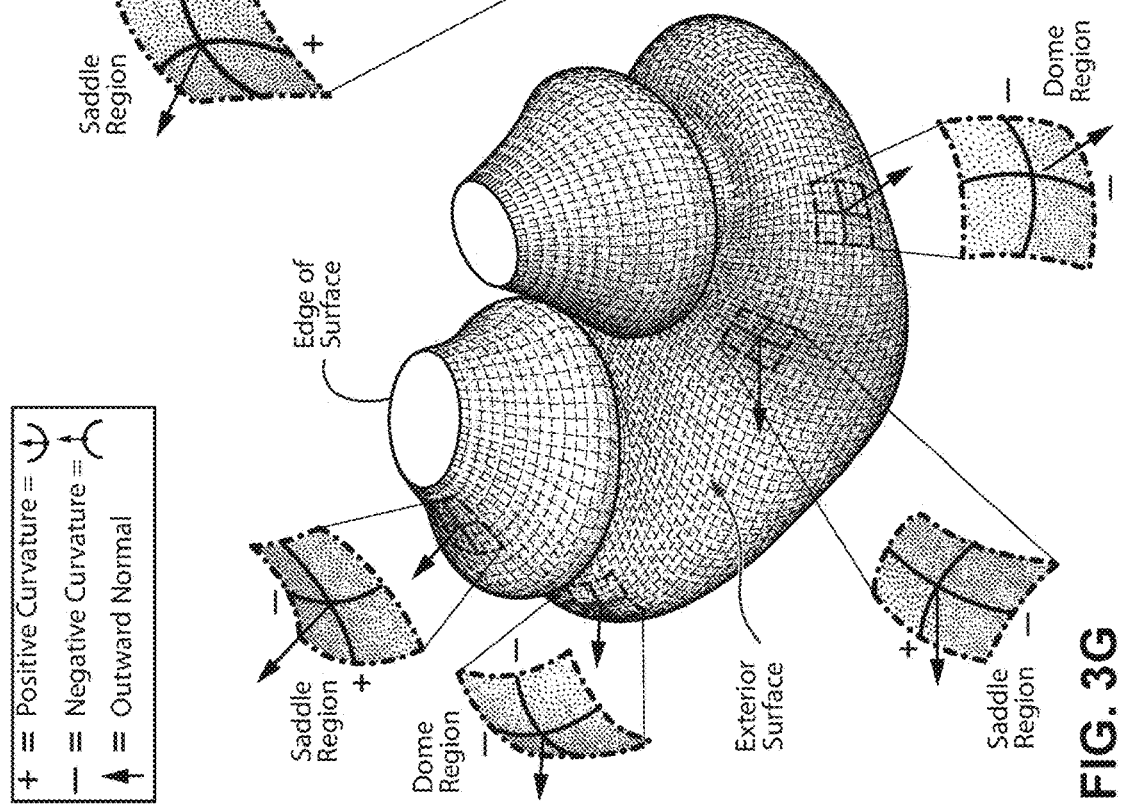

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
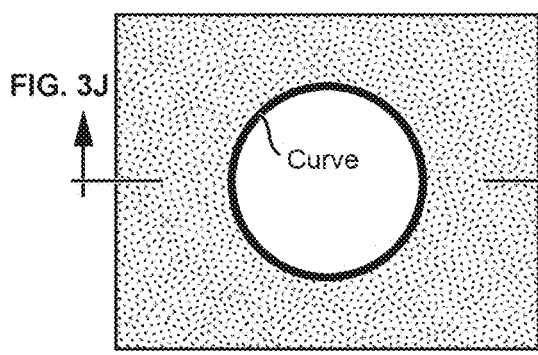

FIG. 3I shows the surface of a structure, with a one dimensional hole in the surface. The illustrated plane curve forms the boundary of a one dimensional hole.

Figure 3K:
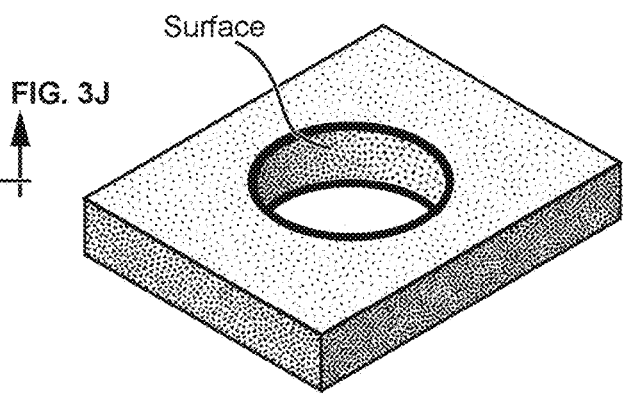
Figure 3J:
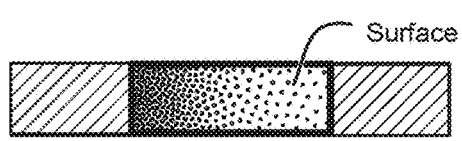

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
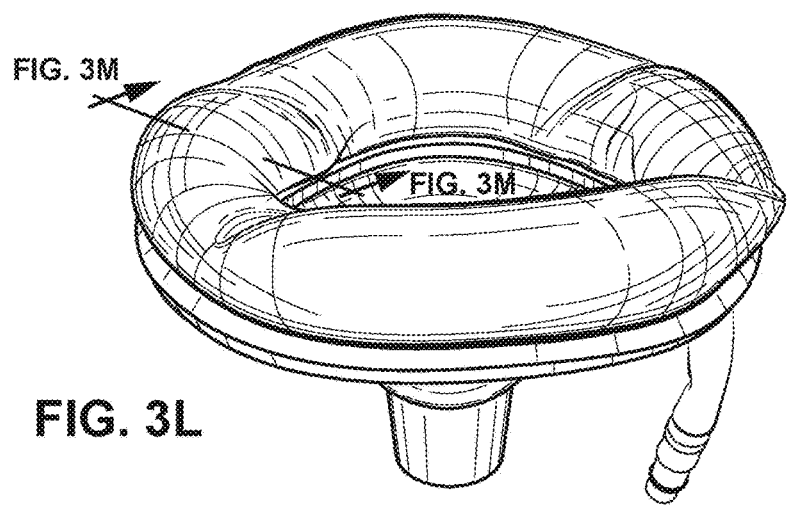

FIG. 3L shows a mask having an inflatable bladder as a cushion.

Figures 3M, 3N:
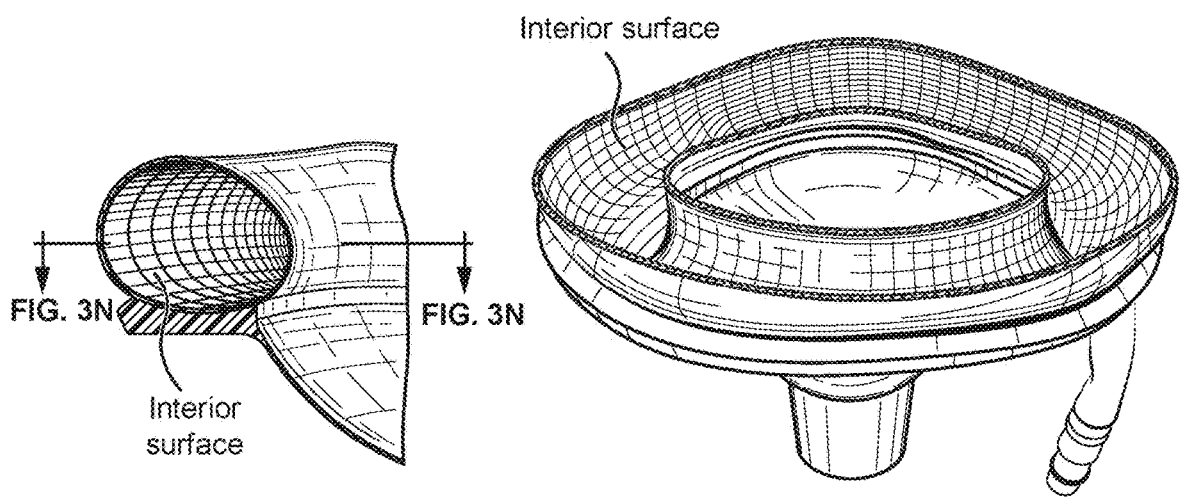

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

Figure 3T:
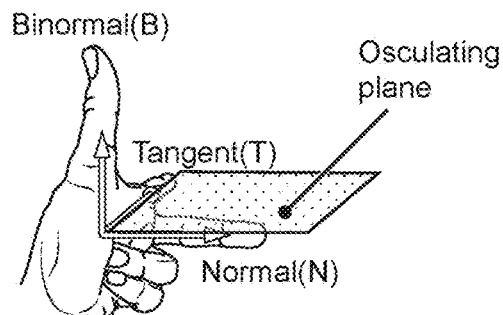
Figure 3T:
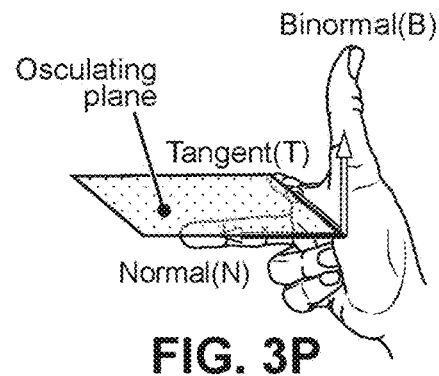
Figure 3T:
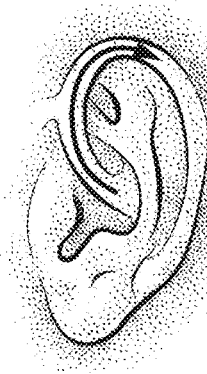
Figure 3T:
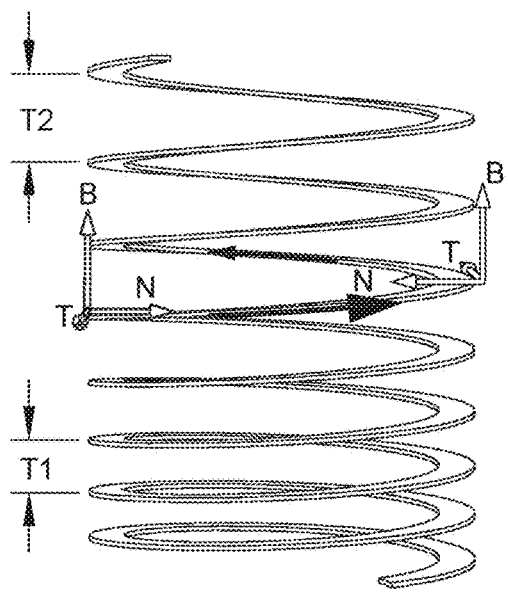
Figure 3T:
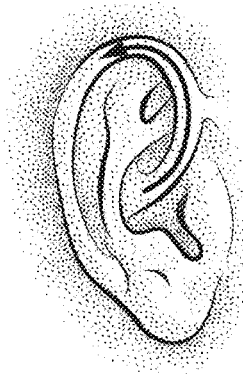
Figure 3T:
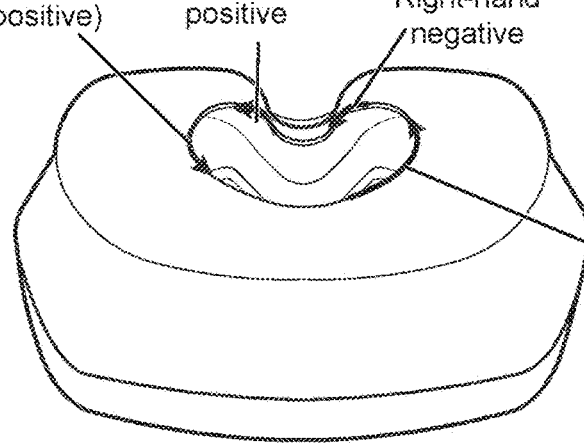

FIG. 3T shows a view of a mask, including the sign of the torsion of the space curve defined by the edge of the sealing membrane in different regions of the mask.

Figure 3U:
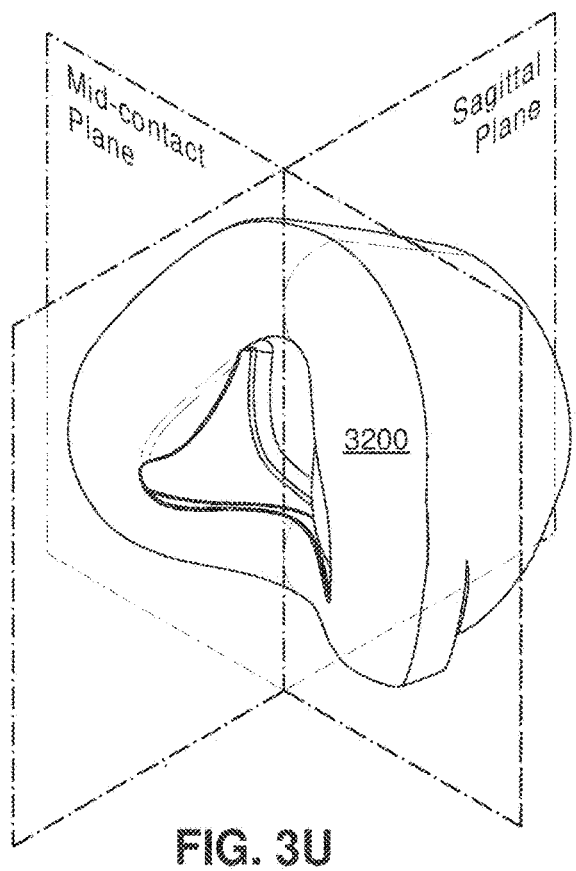

FIG. 3U shows a view of a plenum chamber (cushion assembly) 3200 showing a sagittal plane and a mid-contact plane.

Figure 3V:
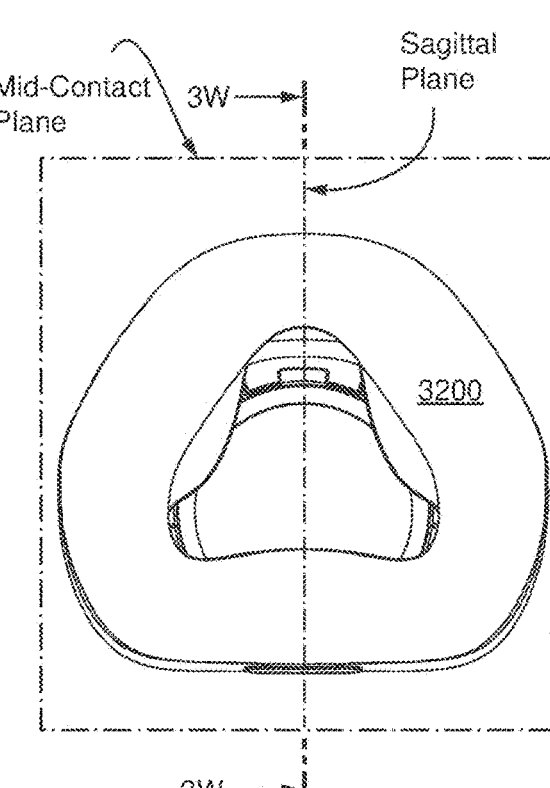

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
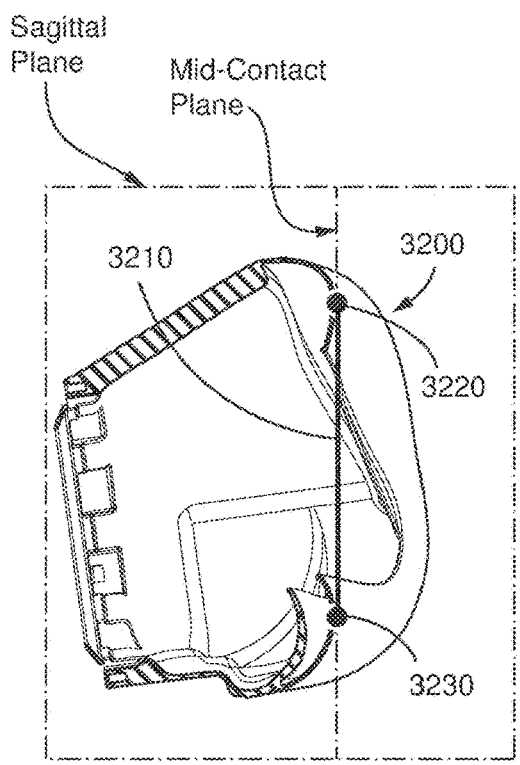

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
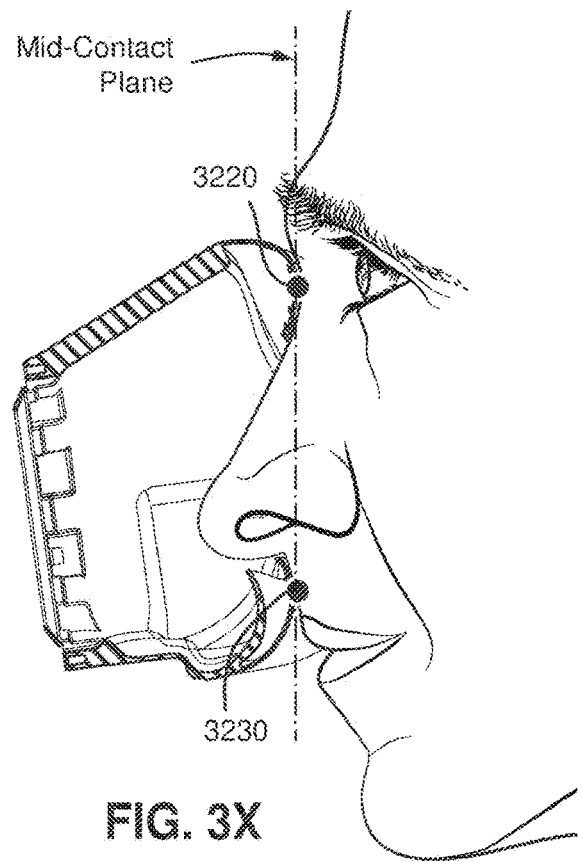

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 3Y:
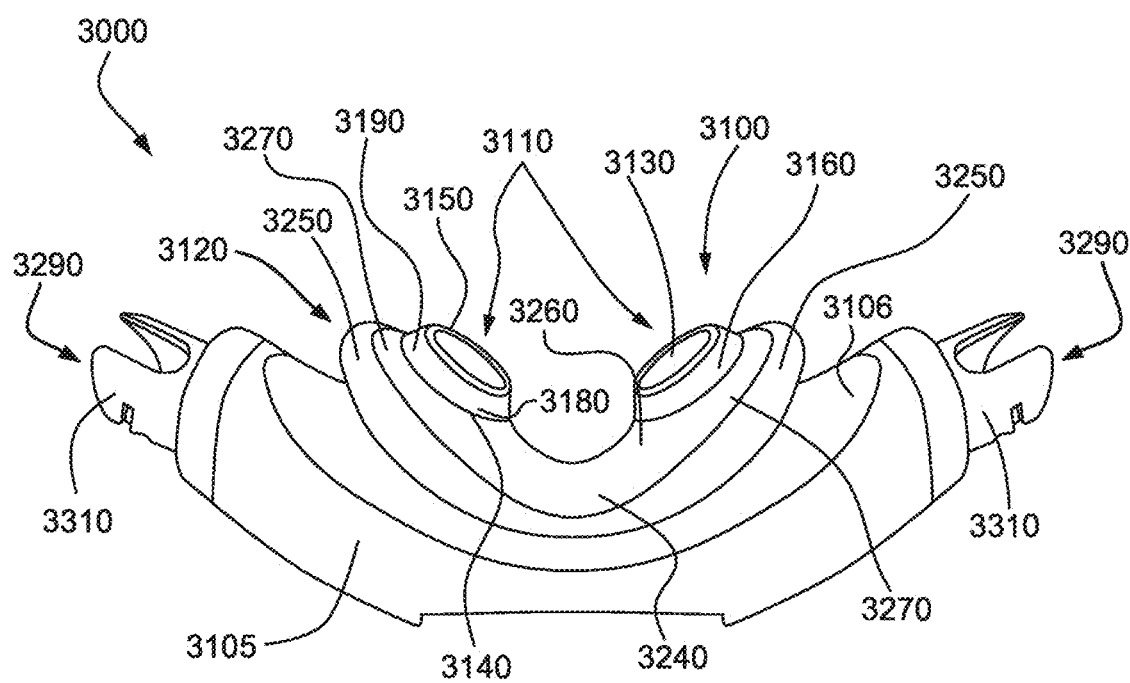

FIG. 3Y depicts an anterior perspective view of a patient interface according to one aspect of the present technology.

Figure 3Z:
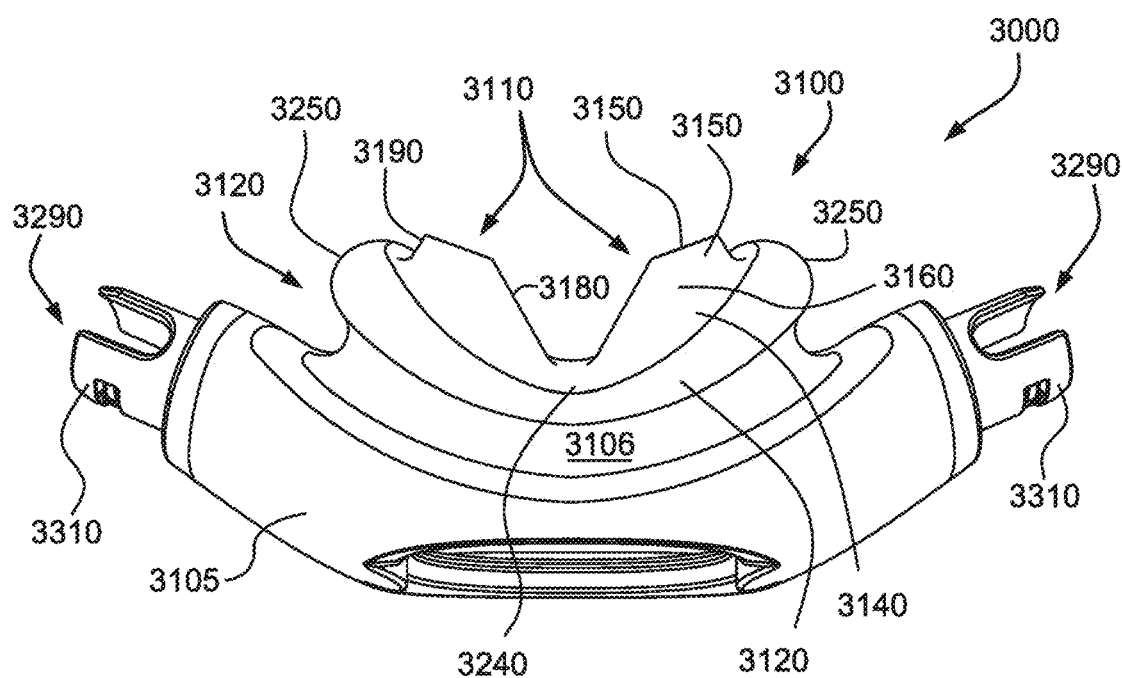
Figure 3A:
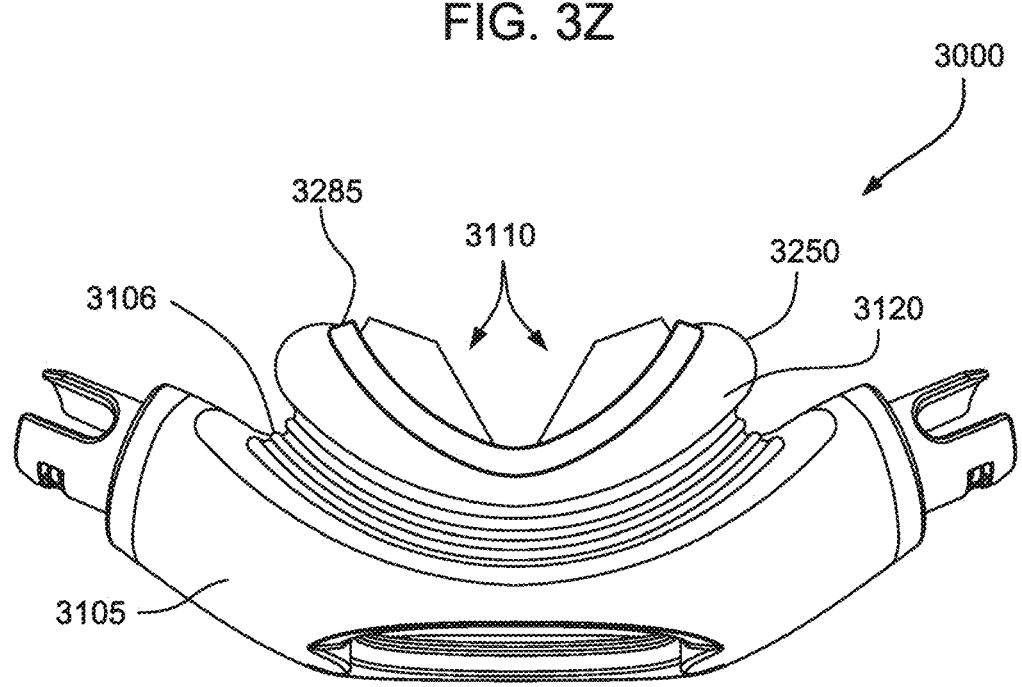
Figure 3B:
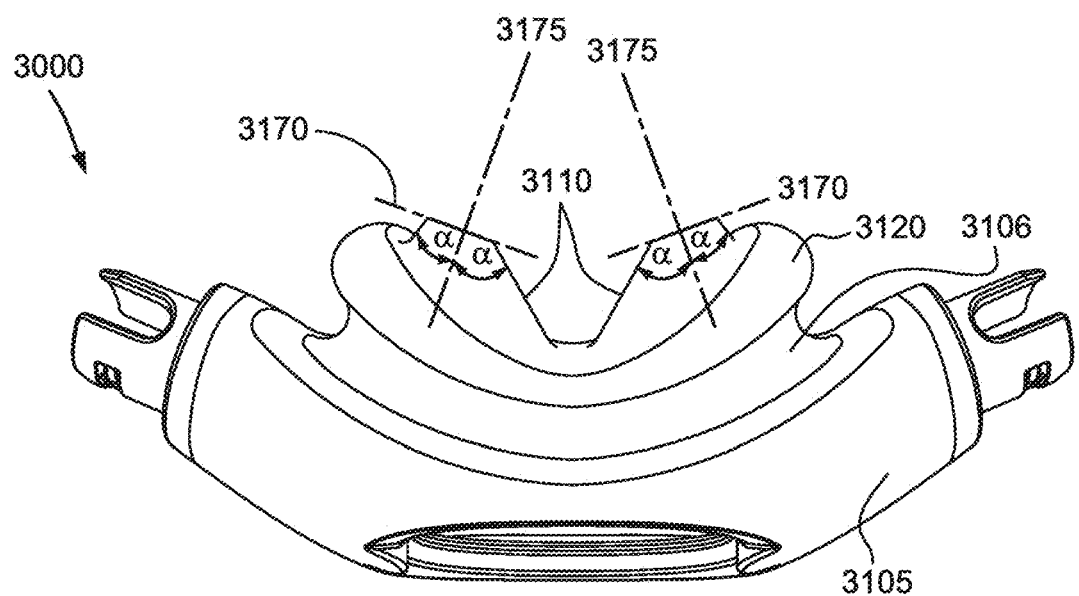
Figure 3C:
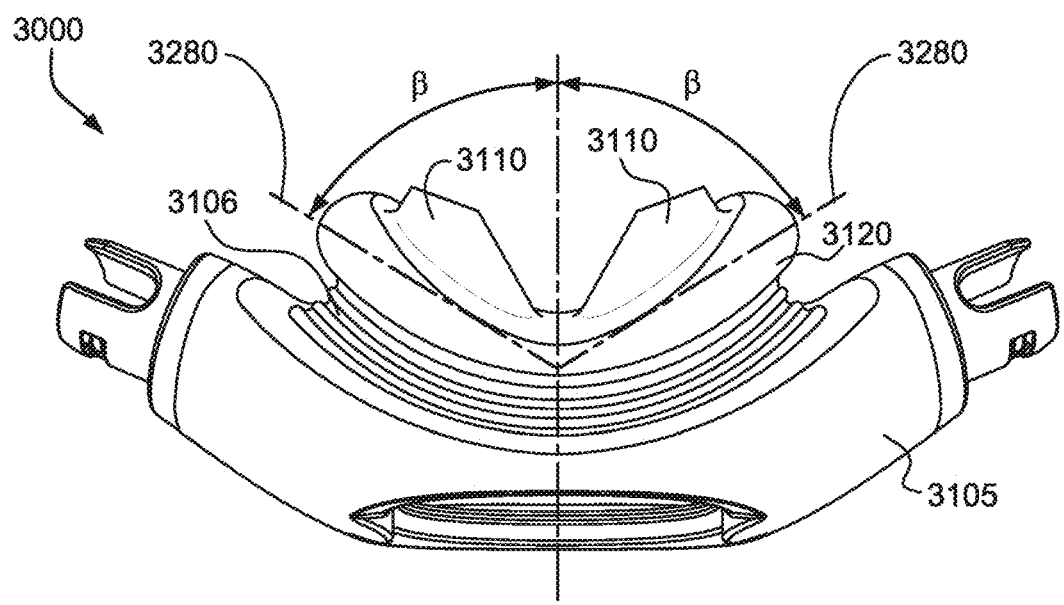
Figure 3D:
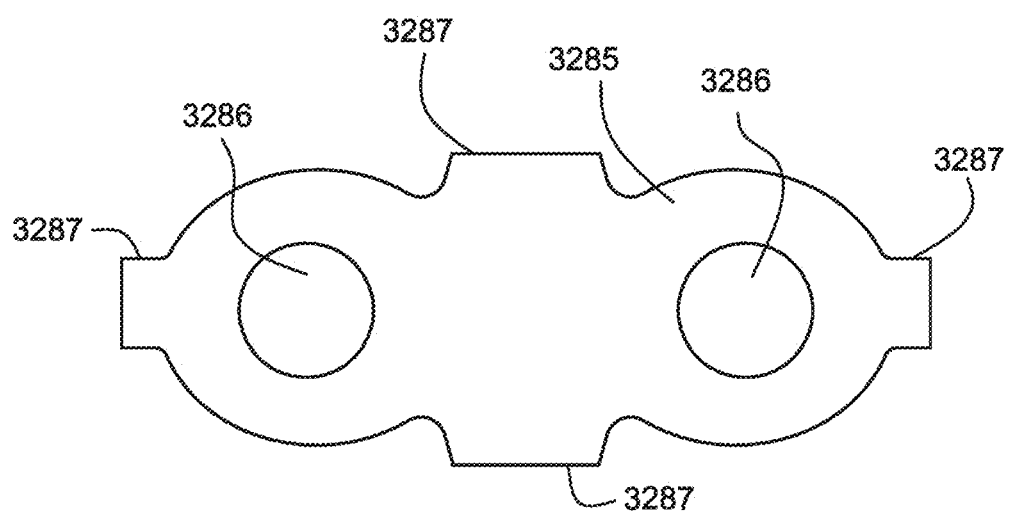
Figure 3E:
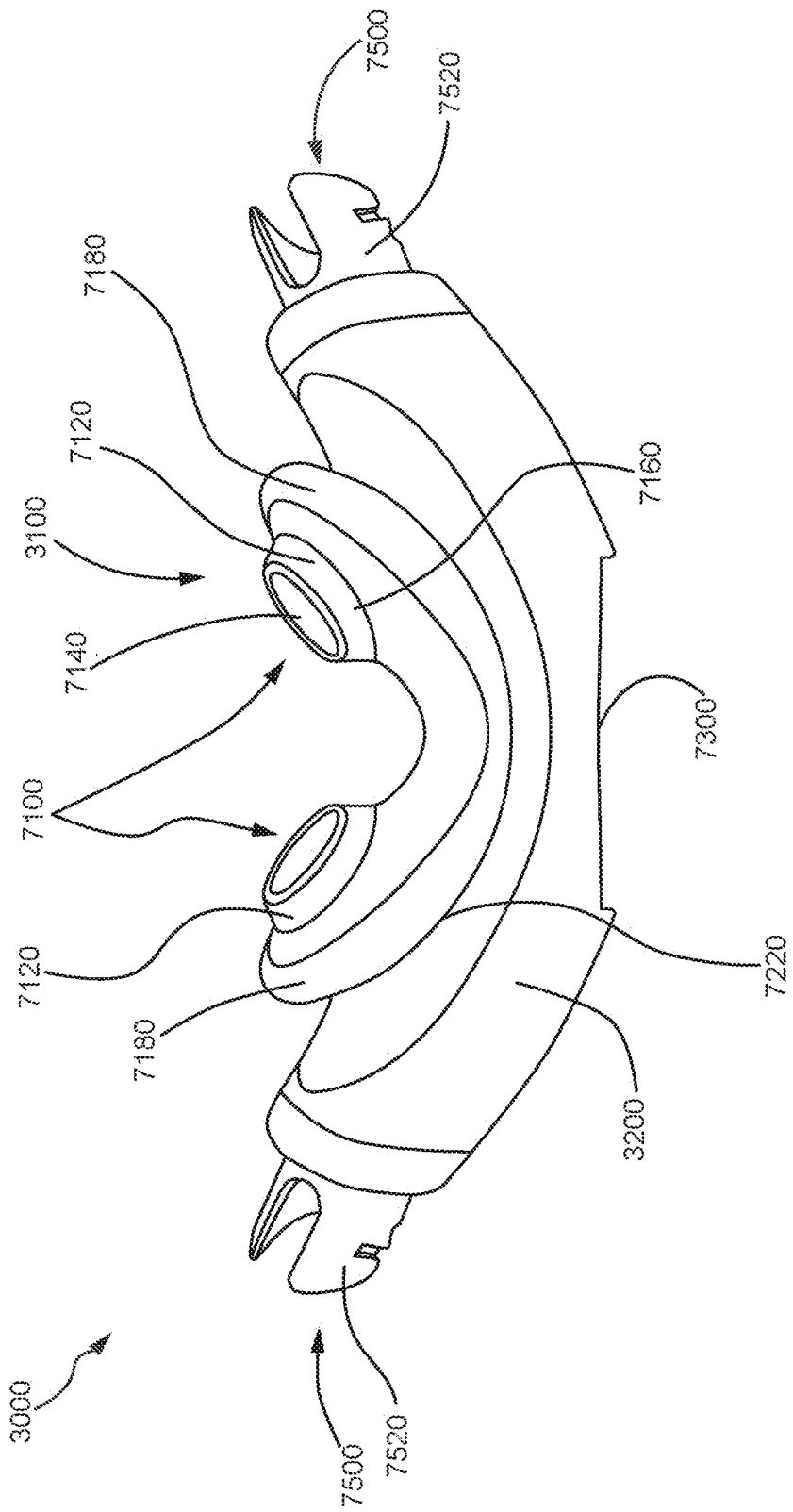
Figure 3F:
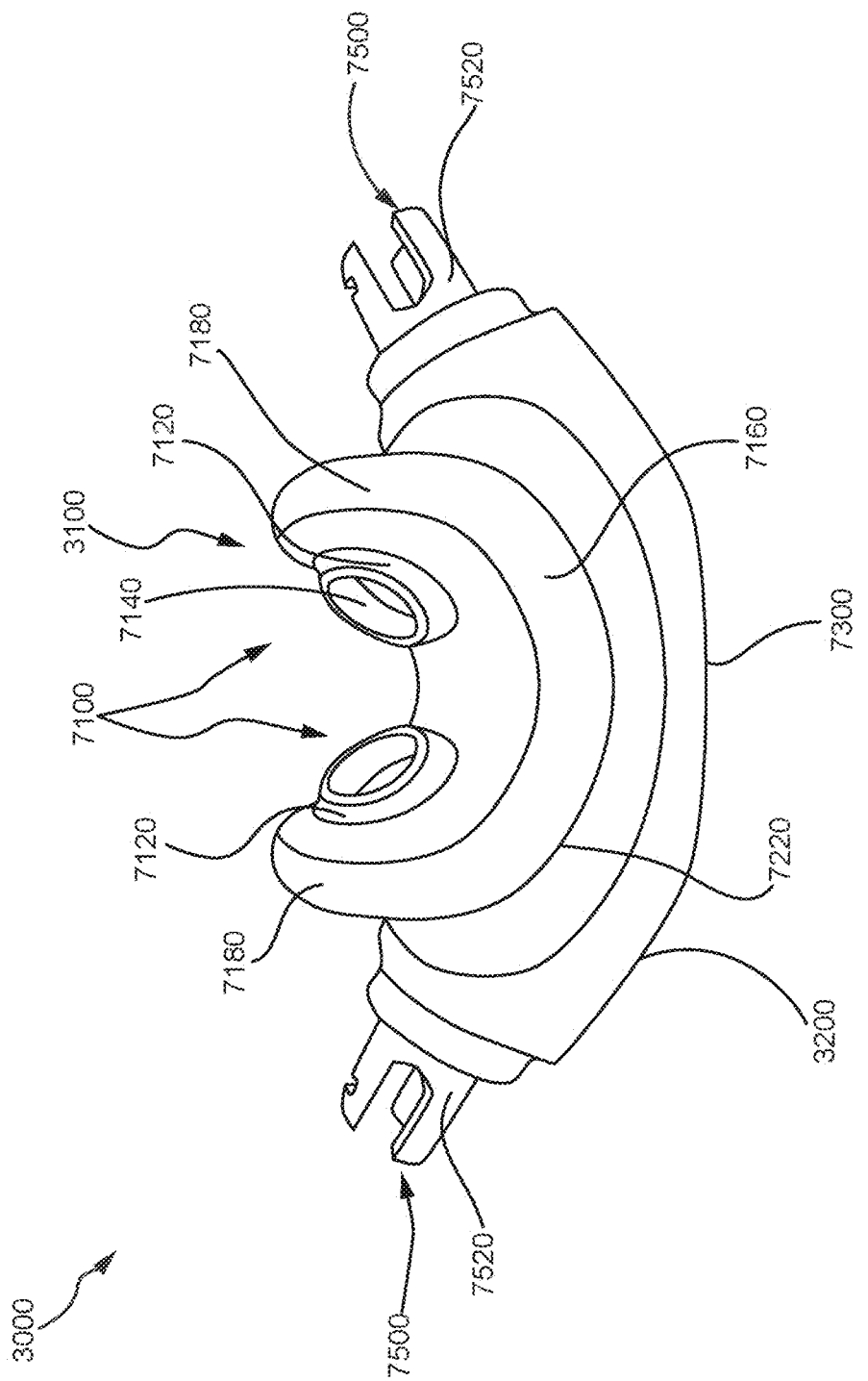

FIG. 3Z depicts an anterior-superior view of a patient interface according to another aspect of the present technology.

FIG. 3AA depicts a side view of a patient interface according to another aspect of the present technology.

FIG. 3BB depicts a side view of a patient interface according to another aspect of the present technology.

FIG. 3CC depicts a side view of a patient interface according to another aspect of the present technology.

FIG. 3DD depicts a top view of a foam layer.

FIG. 3EE depicts an anterior perspective view of a patient interface according to another aspect of the present technology.

FIG. 3FF depicts an anterior-superior view of the patient interface of FIG. 3EE.

4.4 RPT Device

Figure 4A:
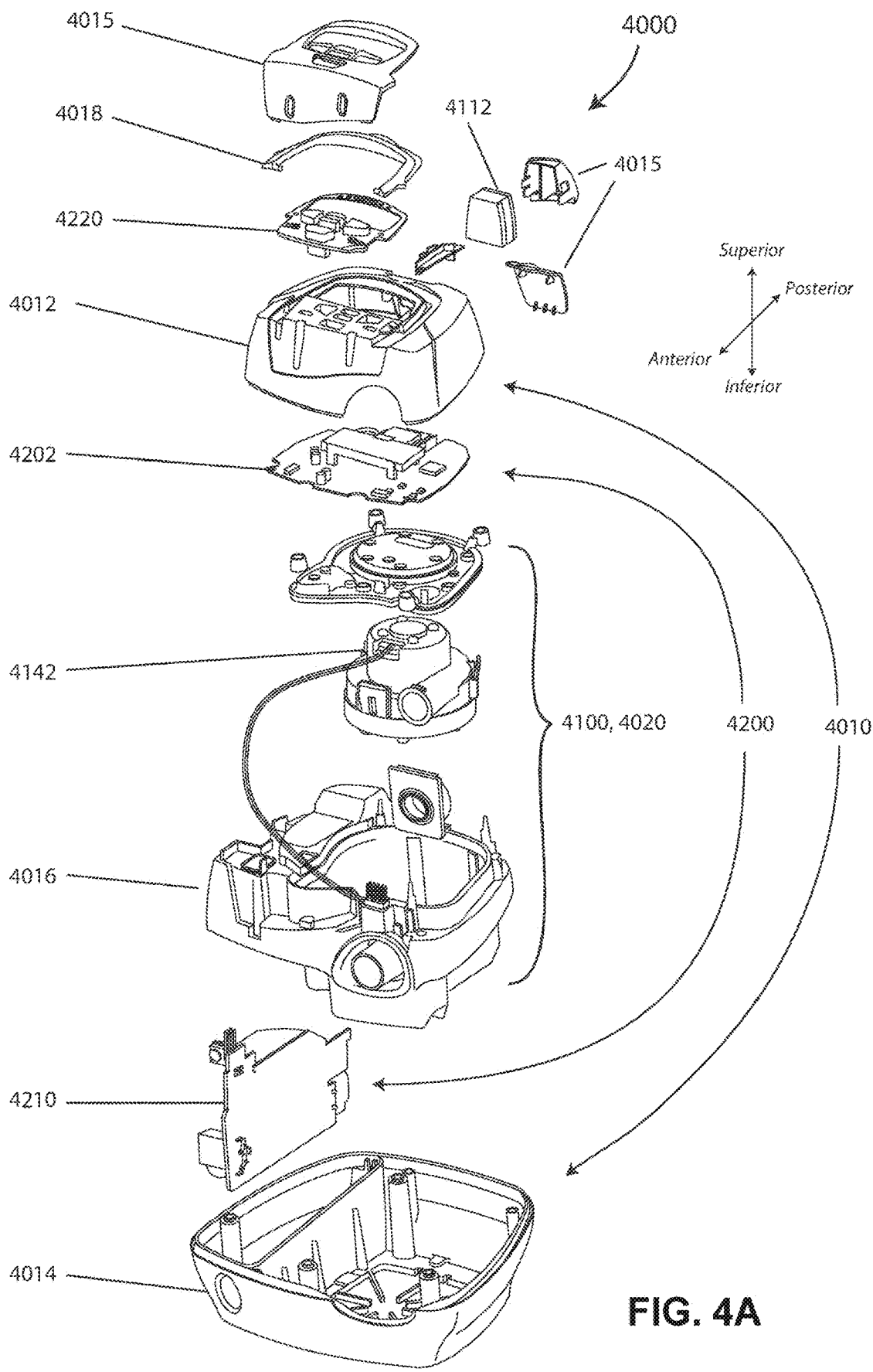

FIG. 4A shows an RPT device in accordance with one form of the present technology.

Figure 4B:
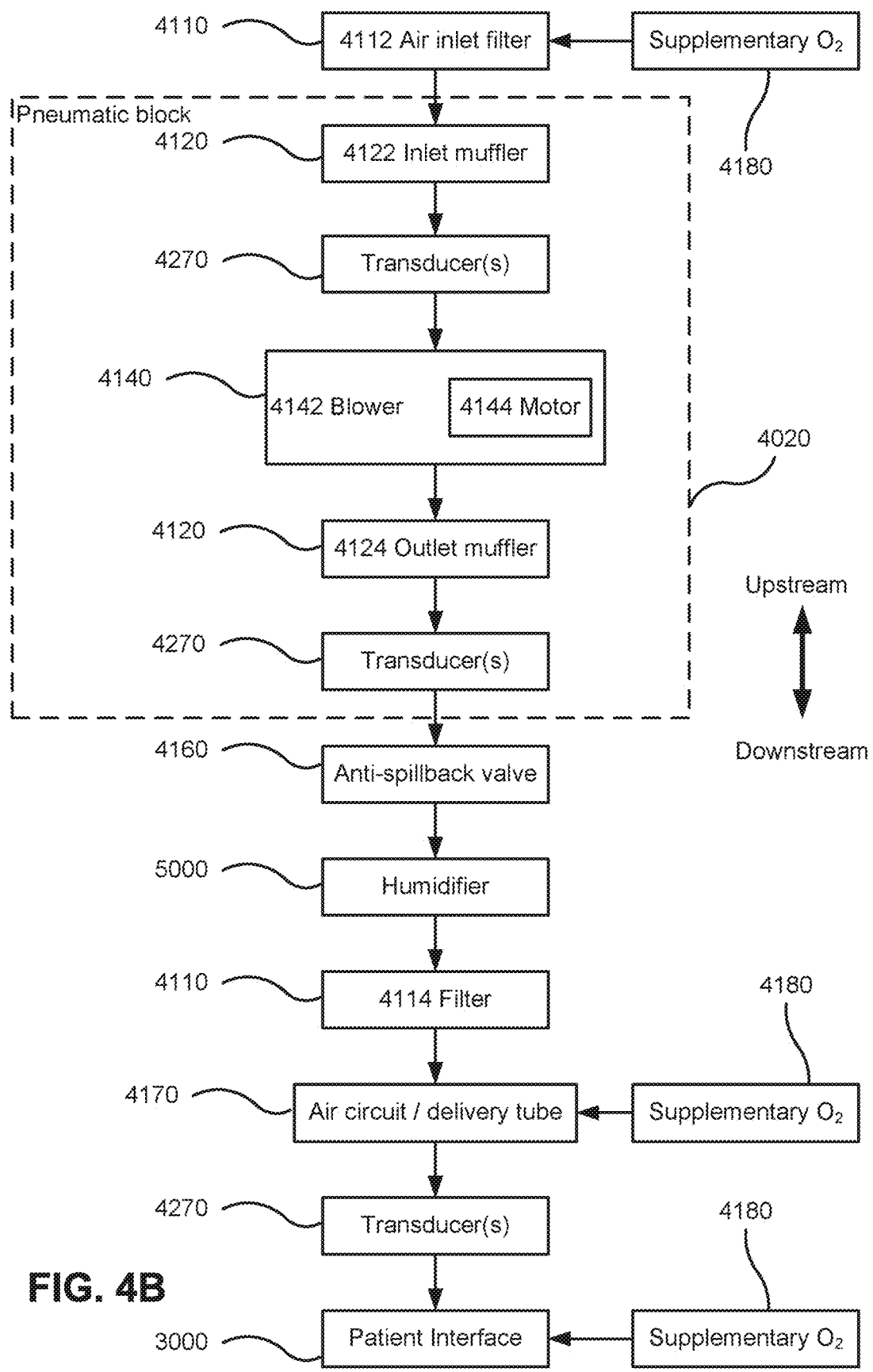

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
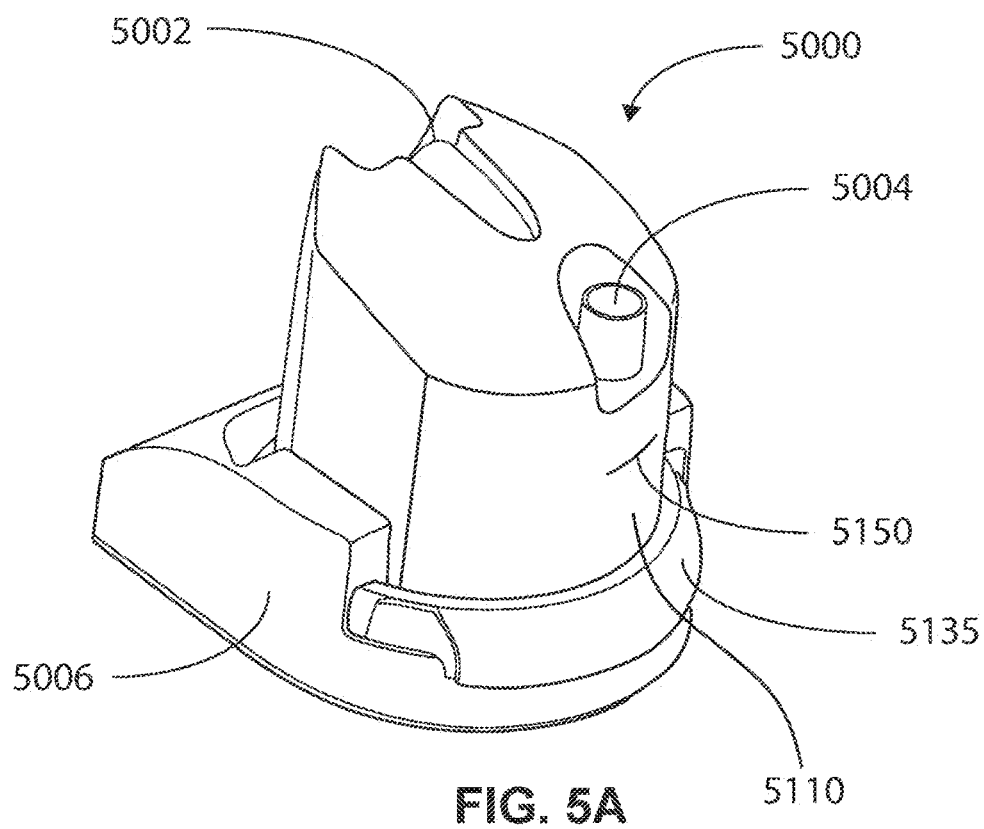

FIG. 5A shows an isometric view of a humidifier in accordance with one form of the present technology.

Figure 5B:
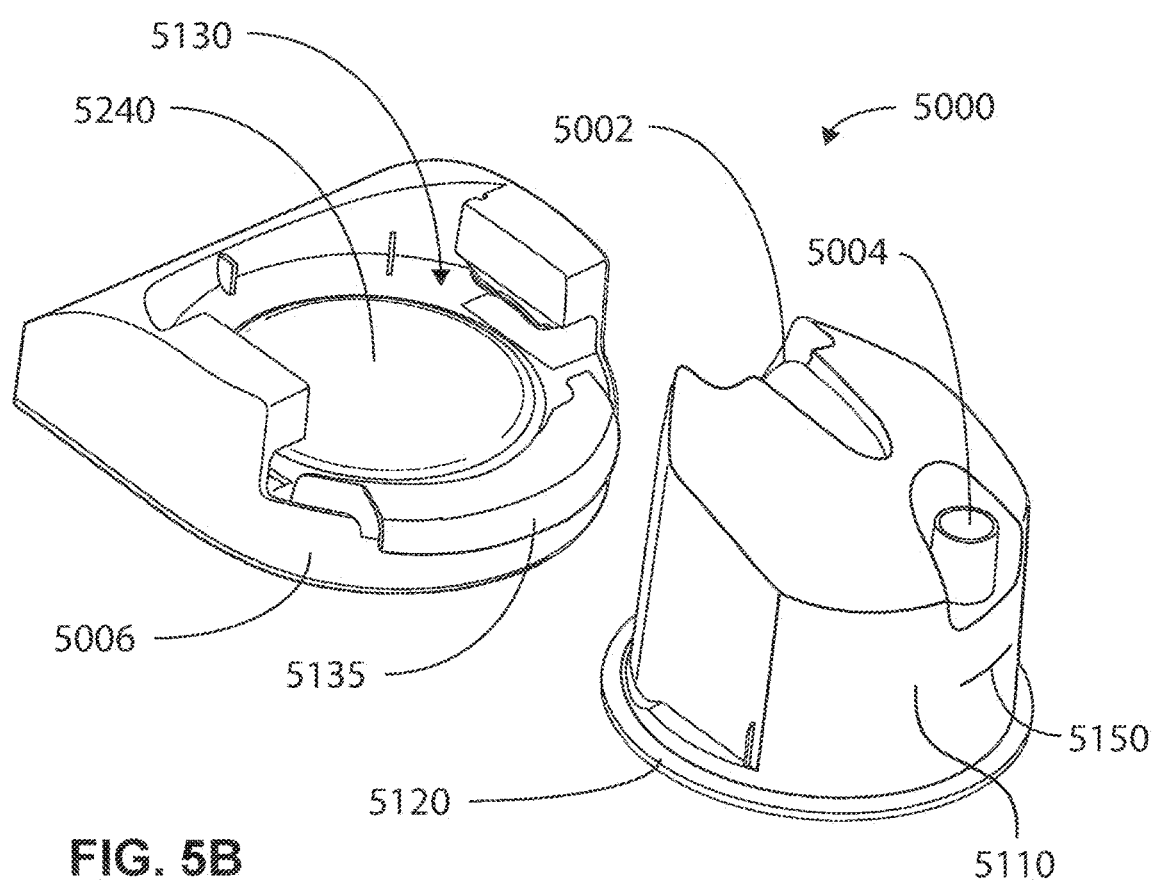

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
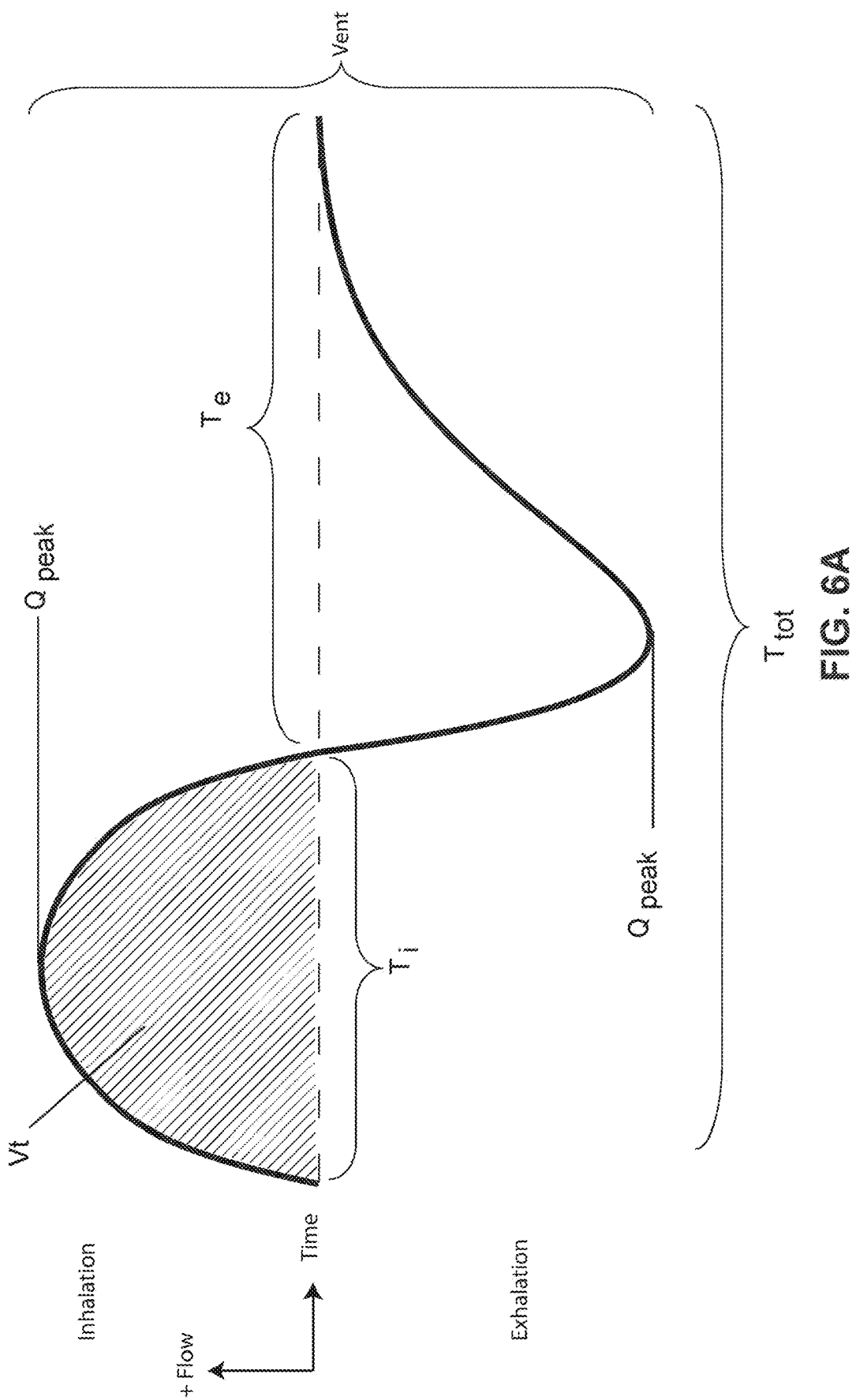

FIG. 6A shows a model typical breath waveform of a person while sleeping.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nasal Seal

FIGS. 3Y through 3CC depict patient interfaces 3000 including seal-forming structures 3100 and plenum bases 3105 according to another aspect of the present technology. A damper or buffer 3106 may be located between the seal-forming structure 3100 and the plenum base 3105 to decouple movement of the seal-forming structure 3100 from the plenum base 3105.

The seal-forming structures 3100 of the patient interfaces 3000 may be a nasal cradle with anchors configured to anchor the nasal cradle to the patient's nostrils. Each seal-forming structure 3100 may include a pair of protrusions 3110 extending from a cradle base 3120. The protrusions 3110 may be constructed and arranged to form a seal with a respective naris of the nose of a patient. Alternatively, the protrusions 3110 may only engage part of the patient's nares and may not form a seal with the nares of the nose of the patient.

The protrusions 3110 may be structured and arranged to, in use, be inserted into, or partly into, a respective one of the patient's nares. Each protrusion 3110 may be hollow and may have an opening 3130 at a terminal end of the protrusions 3110. Each projection 3110 may be configured to allow a continuous pressurized flow of respiratory gas to pass therethrough such that, when the patient interface 3000 is donned, the pressurized flow of respiratory gas may pass into the patient's nares.

In certain forms of the technology, each protrusion 3110 may be configured to extend partly into a respective one of the patient's nares. For example, each protrusion 3110 may be structured and arranged to engage and seal (or only engage), in use, with an inner peripheral edge of the respective naris. The height of each protrusion 3110 may be less than a conventional nasal pillow patient interface. For example, the height of each protrusion 3110 from the cradle base 3120 may be less than 2 cm. It is contemplated that the height of each protrusion 3110 from the cradle base 3120 may be less than 1 cm. It is further contemplated that the height of the protrusion 3110 from the cradle base 3120 may be less than 0.5 cm. The end (or edge) of each protrusion 3110 that forms the opening 3130 may be configured to engage and seal (or only engage) against an inner peripheral edge of the respective naris.

Each protrusion 3110 may have a base end 3140 adjacent the cradle base 3120 and an outlet end 3150 opposite the base end 3140. The opening 3130 may be at the outlet end 3150. Given the hollow structure of the protrusion 3110, the peripheral wall 3160 of the protrusion 3110 may form a gas passage for the pressurized flow of respiratory gas.

Each protrusion 3110 may be tapered so that the footprint of the protrusion 3110 is largest at the base end 3140 and is smallest at the outlet end 3150. The structure of the protrusion 3110 may be different from a conventional nasal pillow by eliminating the thinner stalk portion between the widest portion and the base that allows substantial flexing and/or bending of the nasal pillow relative to its base Eliminating the stalk portion may minimize relative movement between the protrusion 3110 and the surface of the cradle base 3120 from which the protrusion 3110 extends, thereby facilitating the anchoring action of the protrusion 3110.

It is contemplated that the protrusion 3110 may have a frusto-conical or similar shape. For example, as shown in FIGS. 3Y and 3Z, the peripheral wall 3160 of the protrusion 3110 may be tapered from the base end 3140 toward the outlet end 3150, while the cross-sectional shape of the protrusion 3110 may be elliptical rather than circular. It is further contemplated that the shape of the protrusion 3110 is not limited to the shape shown in FIGS. 3Y and 3Z. For example, the cross-sectional shape of the protrusion 3110 may be circular, rectangular, triangular, or any combination thereof. It is contemplated that the cross-sectional shape may be open on at least one side. For example, the cross-sectional shape may be C-shaped. For configurations in which the cross-sectional shape is open on at least one side, the protrusions 3110 may not form part of the gas flow path. Instead, the protrusions 3110 may merely act to anchor the seal-forming structure 3100 to the patient's nose.

Alternatively, the peripheral wall 3160 of the protrusion 3110 may not be tapered, and the footprint of the protrusion 3110 is consistent from the base end 3140 to the outlet end 3150. It is also contemplated that (depending on the cross-sectional shape of the protrusion 3110) there may be more than one peripheral wall 3160.

As shown in FIG. 3BB, the opening 3130 may extend along a plane 3170. In addition, the protrusion 3110 may have a longitudinal axis 3175 that is perpendicular to the plane 3170 and extends through the base and outlet ends 3140, 3150 of the protrusion 3110. In addition, the peripheral wall 3160 may be tapered at an angle α relative to the longitudinal axis 3175. The angle of taper α may vary in a direction perpendicular to the longitudinal axis 3175. For example, the angle of taper α of the peripheral wall 3160 may be smallest at a centrally facing side 3180 of the protrusion 3110 (i.e., the side of the protrusion 3110 closest to the other protrusion 3110). At the same time, the angle of taper α of the peripheral wall 3160 may be largest at an outwardly facing side 3190 of the protrusion 3110 (i.e., the side of the protrusion 3110 furthest from the other protrusion 3110). In this configuration, the length of the peripheral wall 3160 from the base end 3140 to the outlet end 3150 may be largest at the centrally facing side 3180 and smallest at the outwardly facing side 3190.

By varying the angle of taper α, the protrusion 3110 and the opening 3130 may be angled relative to the portion of the cradle base 3120 from which the protrusion 3110 extend. The portion of the cradle base 3120 from which the protrusion 3110 may be angled relative to the opening in the patient's nostrils. Thus, angling the protrusion 3110 and the opening 3130 relative to the cradle base 3120 may allow for the protrusion 3110 to be aligned with the patient's nostril so that the entirety of the outlet end 3150 is received within the patient's nostril.

Alternatively, the angle of taper α may be consistent in the direction perpendicular to the longitudinal axis 3175. In this configuration, the length of the peripheral wall 2160 from the base end 3140 to the outlet end 3150 may be the same at the centrally facing side 3180 and the outwardly facing side 3190.

It is contemplated that the opening 3130 may have an elliptical shape, which may more easily conform to the shape of the patient's nares. However, it should be understood that the opening 3130 may be any other shape such as, for example, a circular shape.

The protrusions 3110 may improve seal stability. For example, in use, the protrusions 3110 may be located in contact with the outer periphery of the patient's nares and may act to position the cradle base 3120 and, by extension, patient interface 3000 in the intended position on the patient's face, and to maintain the patient interface 3000 in that position during use. In other words, the protrusions 3110 may be configured to prevent the patient interface 3000 from moving laterally across the patient's face during use.

To perform its function of anchoring the cradle base 3120 to the patient's nostrils, each protrusion 3110 may need to only engage the rim of the opening to the patient's nasal airways. Thus, the protrusion 3110 may be only long enough to engage the rim of the opening to the patient's nasal airway or the immediate vicinity thereof. In other words, the protrusions 3110 may be designed to not penetrate as far into the patient's nasal passages as conventional nasal prongs or even conventional nasal pillows.

It may be preferable for the protrusions 3110 to not extend beyond (or far beyond) the rims of the openings of the patient's nasal airways to allow for openings 3130 at the ends of the protrusions 3110 with increased areas. In particular, the patient's nasal airways decrease in size as they extend into the patient's nose. Thus, in order to fit within the patient's nasal airways, conventional nasal prongs must decrease in diameter toward their distal ends, thereby decreasing the size of the openings at the distal ends of the nasal prongs. By limiting the extent to which the protrusions 3110 extend into the patient's nasal airways, the openings 3130 at the ends of the protrusions 3110 may be greater in size than would otherwise be the case for conventional nasal prongs. Increasing the size of the openings 3130 may decrease flow restrictions and may improve breathing comfort, while minimizing jetting.

Alternatively, the protrusions 3110 may be designed to penetrate as far into the patient's nasal passages as a conventional nasal prong or nasal pillow (i.e., beyond the immediate vicinity of the rim of the opening to the patient's nasal airways.

It is contemplated that the cradle base 3120 and the protrusions 3110 may be formed from the same material and, in certain forms, they may be formed in one-piece, for example they may be integrally moulded. It is further contemplated that the protrusions 3110 and the cradle base 3120 may be made of a flexible material such as, for example, silicone.

The cradle base 3120 may include a central portion 3240 between a pair of lateral portions 3250. Each protrusion 3110 may be located on a respective lateral portion 3250 so that the protrusions 3110 are on opposite sides of the central portion 3240. In addition, the cradle base 3120 may include a sealing surface 3260 that spans the space between the protrusions 3110 and surrounds the base ends 3140 of the protrusions 3110. Thus, a portion of the sealing surface 3260 of the cradle base 3120 may extend beyond the footprints of the protrusions 3110 and may form a rim 3270 around the protrusions 3110. The sealing surface 3260 may have a size and orientation such that, when the patient interface 3000 is donned, the sealing surface 3260 (and the rim 3270) may engage the patient's skin and seal against a lateral and/or inferior part of the patient's nasal alar.

Thus, the patient interface 3000 may form first and second seals with the patient's nose (e.g., a first seal between the interior walls of the patient's nares and the protrusions 3110 and a second seal between the sealing surface 3260 (and the rim 3270) and the outside of the patient's nose. This may improve the quality of the overall seal between the patient interface 3000 and the patient's face (or nose) and may also stabilise the seal-forming structure in use, thereby reducing the risk of the overall seal being compromised during use.

The cradle base 3120 may be flexible and may have a general cradle, cup, U shape, or V shape that may cradle the patient's nose during use. The flexibility of the cradle base 3120 may allow for the lateral portions 3250 to flex relative to the central portion 3240 so that the lateral portions 3250 (and the protrusions 3110) may be movable toward and away from each other.

As can be seen in FIG. 3CC, the lateral portions 3250 may be oriented at an angle β relative to a plane 3280 that bisects the patient interface 3000 between the protrusions 3110. At rest (or when not engaged with the patient's nose) the lateral portions 3250 may be oriented at a preset (or rest) angle β. However, when the patient dons the patient interface 3000, the patient's nose may cause the lateral portions 3250 (with the protrusions 3110) to flex outwardly, thereby increasing the angle β. The cradle base 3120 may have an elastic characteristic that biases the lateral portions 3250 toward the preset angle β. The biasing force may cause the lateral portions 3250 to press against (or pinch) the patient's nose, thereby maintaining the seal against the patient's nose and stabilising the patient interface 3000 on the patient's face.

It is contemplated that the cradle base 3120 may be hollow. It is further contemplated that the material of the cradle base 3120 may be expandable and/or flexible so that supplying the interior of the cradle base 3120 with pressurized respiratory gas may inflate the cradle base 3120 (i.e., expand the chamber within the cradle base 3120. The inflation of the cradle base 3120 may cause the sealing surface 3260 to be forced against the patient's nose, which may maintain the seal against the patient's nose and may help stabilise the patient interface 3000 on the patient's face.

It is contemplated that different cradle bases 3120 may be sized differently so that cradle bases 3120 of different sizes may have different rest angles β. Utilizing different sizes of cradle bases 3120 and different rest angles β may allow for more design flexibility to cater to patients with noses and/or faces of different sizes and/or shapes. For example, a cradle base 3120 with a larger rest angle β may be more suited to patients with larger, wider and/or flatter noses.

As shown in FIGS. 3AA and 3DD, the seal-forming structure 3100 may optionally include a foam layer 3285 on the sealing surface 3260. The foam layer 3285 may span the entire sealing surface 3260 and may include openings 3286 for the protrusions 3110. The foam layer 3285 may increase the comfort of the seal-forming structure 3100 and may be made of open cell or closed cell foam. It is contemplated that the seal-forming structure 3100 may include the foam layer 3285 without the underlying sealing surface 3260. It is further contemplated that the foam layer 3285 may be replaced with a layer made of textile material. Alternatively, the foam layer may be enveloped within a skin made of textile material. Each of these materials are known to enhance tactile comfort when compared to elastomeric silicone.

The foam layer 3285 may be configured to support the seal between the patient interface 3000 and the patient's face. For example, the foam layer 3285 may be adapted to provide a compression seal to the user's face. The compression seal provided by the foam layer 3285 may work in combination with the underlying sealing surface 3260 to provide an improved seal, wherein the underlying sealing surface 3260 may bias the foam layer towards the users face when the seal-forming structure 3100 is internally pressurised. The sealing mechanism may function by a combination of compression of the foam material provided in the foam layer 3285 and may be further supported by internal pressurisation of the seal-forming structure 3100. The foam layer 3285 may also increase the patient's comfort.

The foam layer 3285 may be permanently attached to the cradle base 3120 or may be removable from the cradle base 3120. It is contemplated that the foam layer 3285 may be secured to the cradle base 3120 by way of a clip, snap, adhesive, a hook and loop arrangement, or bonding. Also, the foam layer 3285 may optionally be in the form of a sleeve that envelops the entirety of the cradle base 3120 with the protrusions 3110 extending through the openings 3286. The foam layer 3285 may optionally have one or more flaps 3287. One part of the securing mechanism (e.g., hook, loop, clip, etc.) may be located on the flap 3287, while the other part of the securing mechanism (e.g., hook, loop, clip, etc.) may be on a corresponding location on the cradle base 3120.

Although FIG. 3DD shows four flaps 3287, any number of flaps 3287 may be used (e.g., 1, 2, 3, 4) depending on what is needed to secure the foam layer 3285 top the cradle base 3120. In addition, the locations of the flaps 3287 are not limited to those shown in FIG. 3DD. The flaps 3287 may be positioned anyway along the perimeter of the foam layer 3285.

It is further contemplated that the foam layer 3285 may be held in place by the protrusions 3110. In particular, the diameter (or footprint) of the openings 3286 may be slightly less than the footprint of the base ends 3140 of the projections 3110 so that the openings 3286 may be stretched by the protrusions 3110 when fitted onto the cradle base 3120 and may be held in place by friction between the protrusions 3110 and the rims of the openings 3286.

It is contemplated that the cradle base 3120 may be generally U-shaped when viewed from an anterior side during use. The cradle base 3120 may have a curvature in an anterior-posterior direction (i.e. in the sagittal plane) that is positive, negative or zero. The positive curvature of the cradle base 3120 in the lateral direction may present the protrusions 3110 to the respective nares while part of the cradle base 3120 between the protrusions 3110 may be positioned further in the anterior direction to avoid contact with the patient's columella.

The cradle base 3120 may be configured such that, in the absence of any forces acting on the cradle base 3120, the cradle base 3120 may have an amount of positive curvature in the lateral direction so that, when donned by the patient, engagement of the cradle base 3120 with the nose may decrease the positive curvature of the cradle base 3120. That is, the 'natural' or 'at rest' curvature of the cradle base 3120 may be greater than the curvature of the cradle base 3120 when donned. In examples where the cradle base 3120 is formed from a resilient material, or is configured to resiliently return to its original shape when not donned, the lateral portions 3250 of the cradle base 3120 may be forced inwardly against the patient's nose when the patient interface 3000 is donned. This may assist in creating a seal against the nose and stabilising the patient interface 3000 in the desired location.

It will be appreciated that different patient interfaces 3000 may comprise cradle bases 3120 with different amounts of positive curvature in their 'at rest' states in order to cater for patients with noses and/or faces of different sizes and/or shapes.

The plenum base 3105 may support the cradle base 3120 and the protrusions 3110. In addition, the plenum base 3105 and the cradle base 3120 may together form a combined plenum chamber that receives the pressurized flow of respiratory gas. A portion of the plenum base 3105 may have a surface that is shaped to be complementary to the surface contour of the face of an average person in use. In some forms, the plenum base 3105 and the seal-forming structure 3100 may be formed from a single homogeneous piece of material (e.g., silicone).

In certain forms of the present technology, the plenum base 3105 may be constructed from a transparent material, e.g. a transparent polycarbonate or silicone material. Alternatively, the plenum base 3105 may be constructed from a translucent material.

In certain forms of the present technology, the plenum base 3105 may be formed of the same material as the seal-forming structure 3100 and may be integrally formed.

One or more positioning and stabilising structure connectors (or headgear connectors) 3290 may be provided to the plenum base 3105. The positioning and stabilising structure connectors 3290 are configured to, in use, connect to the positioning and stabilising structure 3300. The positioning and stabilising connectors 3290 may be located on opposing lateral sides of the plenum base 3105. It is contemplated that the positioning and stabilising structure connectors 3290 may comprise clips, buckles or any other connector able to connect to, or be connected to, a positioning and stabilising structure 3300, for example headgear straps and headgear conduits.

The positioning and stabilising structure connectors 3290 may be in the form of or may comprise inlet tubes 3310 projecting from the lateral sides of plenum base 3105. The inlet tubes 3310 may be configured to receive pressurized respiratory gas from one or more air delivery tubes and/or one or more conduits in the positioning and stabilising structure (or headgear) 3300. It is contemplated that connecting the inlet tube 3310 to an air delivery conduit may simultaneously connect the plenum base 3105 (as well as the patient interface 3000) to the positioning and stabilising structure (or headgear) 3300 when the positioning and stabilising structure (or headgear) 3300 includes headgear conduits.

The damper or buffer 3106 may intervene between the cradle base 3120 and the plenum base 3105. The damper or buffer 3106 may decouple movement of the cradle base 3120 (as well as movement of the protrusions 3110) from the plenum base 3105. The damper or buffer 3106 may completely surround the cradle base 3120 or may only partly surround the cradle base 3120. It is contemplated that the lateral portions 3250 of the cradle base 3120 may extend beyond the damper or buffer 3106. In addition, the damper or buffer 3106 may be in the form of a channel (FIG. 3Z), concertina (FIG. 3AA), bellows, spring, or other structure between the cradle base 3120 and the plenum base 3105 capable of decoupling movement of the cradle base 3120 from the plenum base 3105.

The buffer or damper 3106 and may absorb side loads acting on the cradle base 3120 before the side loads are transferred to the plenum base 3105. It is contemplated that the buffer or damper 3106 may allow the lateral portions 3250 of the cradle base 3120 to flex or move independently of the plenum base 3105. It is further contemplated that the plenum base 3105 with the buffer or damper 3106 may inflate due to internal pressurization within the plenum chamber formed by the cradle base 3120 and the plenum base 3105. The inflation of the plenum base 3105 and the channel 3320 may bias the protrusions 3110 and the sealing surface 3260 against the patient's nose, thereby further supporting the seals formed by the protrusions 3110 and the sealing surface 3260.

In addition, the lateral portions 3250 of the cradle base 3120 may project away from the plenum base 3105 and the buffer or damper 3106 so that only the central portion 3240 is directly attached to the plenum base 3105. It is contemplated that part of the lateral portions 3250 closest to the central portion 3240 may also be directly attached to the plenum base 3105. As such, at least part of the lateral portion 3250 may be separated from the plenum base 3105 and the buffer or damper 3106 so that a surface 3330 of the lateral portion 3250 opposite the sealing surface 3260 may face the buffer or damper 3106 and/or a surface of the plenum base 3105. The flexibility of the buffer or damper 3106 may allow the surface 3330 to move toward and away from the surface of the plenum base 3105. Such flexibility of movement may help maintain the seal against the patient's nose during use.

The buffer or damper 3106 may be an independent component.

Alternatively, the buffer or damper 3106 may form part of the cradle base 3120 of the seal-forming structure 3100 and/or a part of the plenum base 3105. As a concertina or bellows structure, the buffer or damper 3106 may form one or more folds. For example, the one or more folds 3340 may be provided in a part of the cradle base 3120 that connects to, and/or is adjacent to, the plenum base 3105. The one or more folds 3340 may also (or alternatively) be provided in a part of the plenum base 3105 that connects to, and/or is adjacent to, the cradle base 3120. As a channel structure, the buffer or damper 3106 may form an indentation in the surface of the plenum base 3105.

As shown in FIGS. 3Y-3CC, the cradle base 3120 may connect to the plenum base 3015 along a generally oval or elongate shaped region that is smaller in extent than the outer extent of the cradle base 3120. In addition, the buffer or damper 3106 may project inwardly toward an interior of the part of the plenum chamber formed by the plenum base 3105. In other forms, the buffer or damper 3106 may project outwardly away from the part of the plenum chamber formed by plenum base 3105. When the buffer or damper 3106 comprises a concertina or bellows structure, parts of the buffer or damper 3106 may project inwardly, while other parts may project outwardly.

The buffer or damper 3106 may act to at least partially decouple movement of the cradle base 3120 from the plenum base 3105 in use. Additionally or alternatively, the buffer or damper 3106 may enable the seal-forming structure 3100 to adapt to the facial structures of different patients. Additionally or alternatively, the buffer or damper 3106 may act like a spring such that, when deformed by a patient donning the patient interface 3000 and the pressing of the cradle base 3120 towards the plenum base 3105, the buffer or damper 3106 may urge the cradle base 3120 towards the patient's face, helping to maintain the seal-forming structure 3100 in sealing engagement with the patient's face. Additionally or alternatively, the buffer or damper 3106 may be configured to inflate, or partially inflate, when pressurised air enters the plenum base 3105 and/or the seal-forming structure 3100. Such inflation may assist in urging the cradle base 3120 towards the patient's face, helping to maintain the seal-forming structure 3100 in sealing engagement with the patient's face.

The plenum base 3105 may include a vent comprising one or more openings. In addition, the patient interface 3000 may not include a mouth seal or cushion (e.g., a cushion configured to seal around the patient's mouth). Also, the buffer or damper 3106 may not be configured to decouple movement between two sealing surfaces. The buffer or damper 3106 may not be configured to decouple movement between a mouth seal and a nasal seal.

5.3.1.3 Nasal Pillows

FIGS. 3EE and 3BB depict another patient interface 3000 including seal-forming structures 3100 according to examples of the present technology. In these examples the seal-forming structures of the non-invasive patient interface 3000 comprise a pair of nasal puffs 7100, which may alternatively be referred to as nasal pillows, each nasal puff or nasal pillow 7100 being constructed and arranged to form a seal with a respective naris of the nose of a patient.

Nasal pillows 7100 in accordance with forms of the present technology comprise protrusions 7120 structured and arranged to, in use, be inserted into, or partly into, a respective one of the patient's nares. Each nasal pillow 7100 has formed therein an opening 7140 configured to allow a continuous flow of air to pass therethrough such that, when the patient interface 3000 is donned, the flow of air passes into the patient's nares.

In certain forms of the technology the protrusions 7120 are each configured to extend partly into a respective one of the patient's nares. For example, each protrusion 7120 is structured and arranged to seal, in use, with an inner peripheral edge of the respective naris. The height of each protrusion 7120 is therefore less than such a protrusion 7120 on a conventional nasal pillows patient interface. The edge of each protrusion 7120 that forms the opening 7140 is configured to seal against an inner peripheral edge of the respective naris.

Each protrusion 7120 may be formed in the shape of a frusto-cone.

In use the protrusions 7120 are located in contact with the outer periphery of the patient's nares and may act to position the patient interface 3000 in the intended position on the patient's face, and to maintain the patient interface 3000 in that position during use.

The protrusions 7120 may be formed such that the openings 7140 are angled in a manner that is sympathetic with the angle of the patient's nares. That is, the angle of the edge of each protrusion 7120 forms openings 7140 having orientations that are aligned with, or substantially aligned with, the plane formed by the inner peripheral edge of the respective naris.

5.3.1.3.1 Seal-Forming Structure with Base Portion

In the example patient interfaces 3000 shown in FIGS. 3EE and 3FF, the nasal pillows 7100 comprise a base portion 7160 to which the protrusions 7120 are provided. The protrusions extend out of a posterior side of the base portion 7160. The base portion 7160 and protrusions 7120 may be formed from the same material and, in certain forms, they are formed in one-piece, for example they are integrally moulded.

As shown in FIGS. 3EE and 3FF, in some forms of the technology, the base portion 7160 comprises lateral extension portions 7180 that extend outwardly from the base of the protrusions 7120 on a lateral side of each protrusion 7120. The lateral extension portions 7180 have a size and orientation such that, when the patient interface 3000 is donned, the lateral extension portions each seal against a lateral or inferior part of one of the patient's nasal ala. This improves the quality of the seal and also stabilises the seal-forming structure in use, reducing the risk of the seal being compromised during use.

The base portion 7160 is formed to have a generally positive curvature in a lateral direction. For example, the base portion 7160 may be generally U-shaped when viewed from an anterior side during use. The base portion may have a curvature in an anterior-posterior direction (i.e. the sagittal plane) that is positive, negative or zero. The positive curvature of the base portion 7160 in the lateral direction presents the protrusions 7120 to the respective nares while the base portion 7160 between the protrusions 7120 is positioned further in the anterior direction to avoid contact with the patient's columella.

The base portion 7160 may be configured such that, in the absence of any forces acting on the base portion 7160, the base portion 7160 has an amount of positive curvature in the lateral direction so that, when donned by the patient, engagement of the base portion with the nose decreases the positive curvature of the base portion 7160. That is, the 'natural' or 'at rest' curvature of the base portion 7160 is greater than the curvature of the base portion 7160 when donned. In examples where the base portion 7160 is formed from a resilient material, or is configured to resiliently return to its original shape when not donned, the lateral portions of the base portion are forced inwardly against the patient's nose when the patient interface is donned. This assists in creating a seal against the nose and stabilising the patient interface in the desired location.

It will be appreciated that different patient interfaces may comprise base portions with different amounts of positive curvature in their 'at rest' states in order to cater for patients with noses and/or faces of different sizes and/or shapes. For example, the base portion 7160 shown in FIG. 3EE has a smaller positive curvature than the base portion 7160 shown in FIG. 3FF and may therefore be more suited to patients with larger, wider and/or flatter noses.

5.3.1.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

In certain forms of the present technology, the plenum chamber 3200 is formed of the same material as the seal-forming structure 3100. In the forms of the technology shown in FIGS. 3EE and 3FF, the plenum chamber 3200 and the seal-forming structure 3100 are integrally formed.

One or more positioning and stabilising structure connectors 7500 may be provided to the plenum chamber 3200. The positioning and stabilising structure connectors 7500 are configured to, in use, connect to the positioning and stabilising structure 3300. In one form the positioning and stabilising structure connectors 7500 may comprise clips, buckles or any other connector able to connect to, or be connected to by, a positioning and stabilising structure 3300, for example headgear straps.

In the form of the technology shown in FIGS. 3EE and 3FF the positioning and stabilising structure connectors 7500 comprise tubes 7520 projecting laterally outwardly, and posteriorly, from the lateral sides of plenum chamber 3200. In forms of the technology in which the positioning and stabilising structure 3300 comprises one or more gas delivery tubes to deliver a flow of air to the plenum chamber (i.e. "conduit headgear") the gas delivery tubes of the positioning and stabilising structure 3300 fluidly connect to the tubes 7520 projecting outwardly from the plenum chamber 3200. Tubes 7520 are fluidly connected to the plenum chamber 3200 to deliver the flow of gas from the gas delivery tubes of the positioning and stabilising structure 3300 to the plenum chamber 3200.

5.3.1.3.3 Decoupling Folds in Seal-Forming Structure/Plenum Chamber

In certain forms of the technology a part of the base portion 7160 of the seal-forming structure 3100 and/or a part of the plenum chamber 3200 may form one or more folds 7220. For example, the one or more folds 7220 may be provided in a part of the base portion 7160 that connects to, and/or is adjacent to, the plenum chamber 3200. Alternatively, the one or more folds 7220 may be provided in a part of the plenum chamber 3200 that connects to, and/or is adjacent to, the base portion 7160. Alternatively, the one or more folds 7220 may form part of a portion connected in between the base portion 7160 and the plenum chamber 3200.

In the forms of the technology shown in FIGS. 3EE and 3FF the patient interface 3000 comprises a single fold 7220 between the base portion 7160 and the plenum chamber 3200. The base portion 7160 connects to the plenum chamber 3200 along a generally oval or elongate shaped region that is smaller in extent than the outer extent of the base portion 7160. This means that the fold 7220 is an inwards fold. In other forms, the one or more folds may comprise an outwards fold. In other forms the one or more folds may comprise at least one inwards and at least one outwards fold, for example in the manner of a concertina or bellows.

In the forms of the technology shown in FIGS. 3EE and 3FF the fold 7220 extends around the entire periphery of the base portion 7160. In other forms, the one or more folds 7220 may only extend around a portion of the periphery of the base portion 7160. That is, the periphery of the base portion 7160 may comprise one or more portions having one or more folds 7220 and one or more portions without folds.

The one or more folds 7220 may act to at least partially decouple movement of the base portion 7160 from the plenum chamber 3200 in use. Additionally or alternatively, the one or more folds 7220 may enable the seal-forming structure 7100 to adapt to the facial structure of a different patients. Additionally or alternatively, the one or more folds 7220 may act like a spring such that, when deformed by a patient donning the patient interface 3000 and pushing the base portion 7160 towards the plenum chamber 3200, the one or more folds 7220 tend to urge the base portion 7160 towards the patient's face, helping to maintain the seal-forming structure 3100 in sealing engagement with the patient's face. Additionally or alternatively, the one or more folds 7220 may be configured to inflate, or partially inflate, when pressurised air enters the plenum chamber 3200 and/or the seal-forming structure 3100. Such inflation may assist in urging the base portion 7160 towards the patient's face, helping to maintain the seal-forming structure 3100 in sealing engagement with the patient's face.

5.3.2 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

5.3.2.1 Headgear Strap(s)

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain of the present technology, a system is provided comprising more than one positioning and stabilising structure 3300, each being configured to provide a retaining force to correspond to a different size and/or shape range. For example the system may comprise one form of positioning and stabilizing structure 3300 suitable for a large sized head, but not a small sized head, and another suitable for a small sized head, but not a large sized head.

5.3.2.2 Gas Delivery Tube(s)

In some forms of the present technology, the positioning and stabilising structure 3300 comprises one or more conduits in the form of gas delivery tubes that deliver pressurised air received from the air circuit 4170 from the RPT device to the patient's airways, for example through the plenum chamber 3200 and seal-forming structure 3100. In these forms, the positioning and stabilising structure 3300 may be referred to as conduit headgear and, as well as delivering pressurised air to the airways, serves to position and stabilise the seal-forming structure 3100 of the patient interface to the appropriate part of the patient's face. In this specification, and unless the context clearly indicates otherwise, the terms "tube" and "conduit" should be understood to be interchangeable. In these forms, the conduit headgear contacts at least a region of the patient's head superior to an otobasion superior of the patient's head. As seen in FIG. 2D, the otobasion superior is the point on the side of the patient's head that gives rise to the upper portion of the ears.

In one example, the tubes may be substantially cylindrical. However, in other examples, the tubes may be formed with a variety of cross-sectional shapes. For example, a substantially D-shaped cross-sectional profile may be used; the flat side of this profile may contact the patient's face when being worn and may be more comfortable than a semi-circular profile.

In some forms of the present technology, the conduit headgear comprises a pair of tubes that deliver pressurised air from the downstream end of the air circuit to the seal-forming structure. As an example, the tubes may be joined at their superior ends to a crown connector that bears a connection port to fluidly engage with the downstream end of the air circuit and forms an integral part of the positioning and stabilising structure of the patient interface. The tubes may be disconnected, for example for cleaning or storage.

In some forms of the present technology, the conduit headgear comprises left and right tubes, which at their inferior ends fluidly engage or otherwise connect to the patient interface 3000 in order to deliver the pressurised air to the seal-forming structure. A connection port to engage with the downstream end of the air circuit 4170 is provided to the superior portion of the conduit headgear, where the two arms of the tube meet. In this example, the conduit headgear is substantially a unitary structure.

In certain examples the connection port is generally located at the crown of the patient when the conduit headgear is being worn. However, it should be appreciated that the connection port may be provided to a different location, subject to the shape of the conduit headgear. For example, rather than meeting across the crown of the patient's head, the tubes may be arranged to meet further back to the posterior of the patient's head. This would place the connection port proximate a part of the posterior of the patient's head, rather than the crown. Alternatively, the connection port may be provided elsewhere, for example to one of the two tubes rather than where they meet.

In certain examples of the present technology, the conduit headgear is formed from a suitably sprung material that provides sufficient stabilising forces that correctly locates the patient interface in a sealing arrangement on the patient's head. In certain other examples, the positioning and stabilising structure comprises a mechanism for connecting a headgear strap or other stabilising component to the headgear tubes. The headgear strap may supplement the stabilising forces provided by the conduit headgear and help correctly locate the patient interface in a sealing arrangement on the patient's head.

In these examples, the headgear strap may be connected directly or indirectly to the headgear tubes. In the case of one form of patient interface, a tab, configured to connect to the back strap, projects away from the tubes in a generally posterior direction. The tabs have slits in them to receive the ends of the strap.

The back strap may be secured to itself after passing through the slits in the tabs, for example, with hook-and-loop fastening material. The back strap therefore is able to be adjusted to fit around different head sizes. In some forms of the technology, more than one tab may be provided to the tubes to provide the patient a range of alternative placement options for the back strap. This may be helpful for ensuring appropriate application of sealing forces to the face.

The tubes of the conduit headgear may be formed from textile, spacer fabric and/or foam materials, in some examples. Portions of the tubes that contact the patient may be formed with textiles or fabrics for greater patient comfort. In some examples, the tubes may be formed of a semi-rigid material such as an elastomeric material, e.g. silicone. In these examples, the tubes may comprise thin sleeves of fabric or textiles wrapped around them. The sleeves may be more comfortable against the patient's face than the tubes without any covering.

In some examples, the tubes of the conduit headgear may have a natural, preformed shape that conforms to the general shape of the patient's head. In some examples, the tubes may have at least some ability to deform if a force is applied to the tubes or conform to a patient's head. For example, the tubes may be generally arcuate or curved in a shape approximating the contours of a patient's head between the top of the head and the nasal or oral region.

Since air can be contained and passed through the tubes of the conduit headgear in order to deliver pressurised air from the air circuit 4170 to the patient's airways, the conduit headgear may be described as being inflatable. It will be understood that an inflatable conduit headgear does not require all its components to be inflatable. For example, when the positioning and stabilising structure comprises the headgear tubes and back strap, the headgear tubes are inflatable and the back strap is not inflatable.

5.3.3 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled CO2 by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

The vent 3400 provided to the plenum chamber 3200 may include a plurality of openings 3402. The openings 3402 may be arranged in two groups that are symmetrical relative to the centreline of the plenum chamber 3200. The plurality of openings 3402 may reduce noise and diffuse the vent flow concentration.

The openings 3402 may be located sufficiently close to the centreline of the plenum chamber 3200 such that the openings 3402 are not blocked when the patient is sleeping on their side. To avoid weakening the chassis at a relatively narrow portion, the openings 3402 may be spaced from the centreline.

The openings 3402 may have a circular profile.

In the examples of patient interfaces shown in FIGS. 3EE and 3FF, a vent 3400 may be provided to an anterior side of the plenum chamber 3200. For example, the plenum chamber 3200 may comprise an opening 7300 on its anterior side that is configured to receive, in use, a vent 3400. The vent 3400 may be provided as a vent module that can be removed and re-inserted into the opening 7300, for example to wash and/or interchange the vent 3400.

5.3.4 Decoupling Structure(s)

In one form the patient interface 3000 includes at least one decoupling structure 3500, for example, a swivel or a ball and socket. The decoupling structure 3500 may be in the form of an elbow. The decoupling structure 3500 may include a swivel that connects to the air circuit 4170 and a patient interface connector that connects to the patient interface 3000. The patient interface connector may permit a tube of the decoupling structure 3500 to rotate relative to the patient interface 3000. The decoupling structure 3500 may also include a vent 3400. The vent 3400 of the decoupling structure 3500 may include at least one opening through a portion of the tube and/or through a portion of the patient interface connector.

In one form of the technology, the decoupling structure may connect in use to the opening 7300 on the anterior side of the plenum chamber 3200.

In another form of the technology, the decoupling structure may connect in use to a connection port 3600 comprised in, or provided to, one or more gas delivery tubes comprised as part of a positioning and stabilising structure 3300, and positioned, in use, adjacent to a region of the patient's head superior to an otobasion superior of the patient's head.

5.3.5 Connection Port

Connection port 3600 allows for connection to the air circuit 4170.

In certain forms of the technology, the connection port 3600 may be the opening 7300 on the anterior side of the plenum chamber 3200. The connection port 3600 may be configured to connect to the air circuit 4170 and/or a decoupling structure 3500, such as an elbow, provided to the air circuit 4170.

In alternative forms of the technology, for example those incorporating a patient interface 3000 such as shown in FIGS. 3EE and 3FF, the patient interface comprises a connection port comprised in, or provided to, one or more gas delivery tubes comprised as part of a positioning and stabilising structure 3300. In such examples, the connection port may be positioned, in use, adjacent to a region of the patient's head superior to an otobasion superior of the patient's head. In such examples, the flow of air is delivered to the seal-forming structure 3100 via the connection port and the gas delivery tubes comprised as part of a positioning and stabilising structure 3300.

5.3.6 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor in accordance with the present technology may be based on a differential pressure transducer, for example, an SDP600 Series differential pressure transducer from SENSIRION.

In one form, a signal representing a flow rate from the flow rate sensor is received by the central controller.

5.4.1.4.2 Pressure Sensor

A pressure sensor in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor is received by the central controller.

5.4.1.4.3 Motor Speed Transducer

In one form of the present technology a motor speed transducer is used to determine a rotational velocity of the motor 4144 and/or the blower 4142. A motor speed signal from the motor speed transducer may be provided to the therapy device controller. The motor speed transducer may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller.

In one form, the input device 4220 may be constructed and arranged to allow a person to select a value and/or a menu option.

5.4.2.3 Central Controller

In one form of the present technology, the central controller is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers 4270, one or more input devices 4220, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5:L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240. (Year? Required?)

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component. A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.8.4 Anatomy
5.8.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Midsagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion.

5.8.4.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space:

Headgear. Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points (for the imaginary person, the straight-line distance would correspond to the distance 'as the crow flies').

5.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S.

With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 Reference Signs List

| | |
|---|---|
| patient | 1000 |
| bed partner | 1100 |
| patient interface | 3000 |
| seal - forming structure | 3100 |
| plenum base | 3105 |
| damper | 3106 |
| protrusion | 3110 |
| cradle base | 3120 |
| opening | 3130 |
| base end | 3140 |
| outlet end | 3150 |
| peripheral wall | 3160 |
| plane | 3170 |
| longitudinal axis | 3175 |
| centrally facing side | 3180 |
| outwardly facing side | 3190 |
| plenum chamber | 3200 |
| chord | 3210 |
| superior point | 3220 |
| inferior point | 3230 |
| central portion | 3240 |
| lateral portion | 3250 |
| sealing surface | 3260 |
| rim | 3270 |
| plane | 3280 |
| buffer or damper | 3285 |

-continued

| | |
|---|---|
| positioning and stabilising structure connectors | 3290 |
| positioning and stabilising structure | 3300 |
| inlet tube | 3310 |
| surface | 3330 |
| vent | 3400 |
| decoupling structure | 3500 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| supplemental oxygen | 4180 |
| electrical components | 4200 |
| PCBA | 4202 |
| power supply | 4210 |
| input device | 4220 |
| transducer | 4270 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| heating element | 5240 |
| nasal puffs/pillows | 7100 |
| protrusion | 7120 |
| opening | 7140 |
| base portion | 7160 |
| lateral extension portion | 7180 |
| one or more folds | 7220 |
| opening | 7300 |
| positioning and stabilising structure connector | 7500 |
| tube | 7520 |

The invention claimed is:

1. A patient interface configured to deliver a pressurized flow of respiratory gas to a patient's airways, the patient interface comprising:
a cradle base configured to engage and form a seal with the patient's nose in use, the cradle base comprising a pair of lateral portions on opposite lateral sides of the cradle base;
two protrusions extending from the cradle base and being configured to be inserted into the patient's nares in use, each of the protrusions having formed therein an opening configured to allow a continuous flow of air therethrough;
a plenum base that, together with the cradle base, forms a plenum chamber; and
a flexible interface between the cradle base and the plenum base that is configured to decouple movement of the cradle base from the plenum base,
wherein the lateral portions of the cradle base extend laterally outward beyond the flexible interface so that there is a gap between the plenum base and at least part of the lateral portions of the cradle base, and
wherein the plenum base and the cradle base are inflatable to force a sealing surface of the cradle base against the patient's nose in use.

2. The patient interface of claim 1, wherein the protrusions are structured and arranged to seal, in use, with an inner peripheral edge of the respective naris.

3. The patient interface of claim 1, wherein the protrusions comprise ends that, in use, seal with an inner peripheral edge of the respective naris.

4. The patient interface of claim 1, wherein the lateral portions of the cradle base extend laterally beyond the two protrusions, the lateral portions of the cradle base respectively being configured to seal against a lateral or inferior part of each of the patient's nasal ala in use.

5. The patient interface of claim 1, wherein the cradle base is configured to be outwardly flexed by the patient's nose when donned by the patient.

6. The patient interface according to claim 1, wherein the protrusions have a frusto-conical shape.

7. The patient interface according to claim 1, wherein the openings of the protrusions are angled relative to a surface of the cradle base from which the protrusions extend.

8. The patient interface according to claim 1, wherein the plenum base comprises a pair of air inlets on opposing lateral sides.

9. The patient interface according to claim 1, wherein the flexible interface comprises a buffer or damper between the cradle base and the plenum base that is configured to decouple movement of the cradle base from the plenum base.

10. The patient interface according to claim 9, wherein the buffer or damper is not configured to decouple movement between two sealing surfaces.

11. The patient interface according to claim 10, wherein the buffer or damper is not configured to decouple movement between a nasal seal and a mouth seal.

12. The patient interface according to claim 1, wherein the patient interface does not comprise a mouth seal.

13. The patient interface according to claim 1, wherein the protrusions do not include stalks.

14. The patient interface of claim 1, wherein the cradle base and the plenum base are both formed from elastomeric material.

15. The patient interface of claim 1, wherein the two protrusions are oriented so that their respective central longitudinal axes intersect each other when the cradle base is in a neutral state.

16. The patient interface of claim 1, wherein the cradle base is configured so that when the cradle base is in a neutral state, the two protrusions are oriented so that their respective central longitudinal axes intersect each other.

17. The patient interface of claim 1, wherein the cradle base is configured so that the lateral portions are oriented at an angle relative to each other when the cradle base is in a neutral state, and wherein the lateral portions are resiliently biased to return toward the angle when the lateral portions are outwardly flexed.

18. The patient interface of claim 17, wherein the cradle base is configured so that the biasing force of the lateral portions causes the lateral portions to press against the patient's nose in use.

19. The patient interface of claim 1, wherein the two protrusions are configured to seal against an interior of the patient's nostrils, and the cradle base is configured to seal against an outer surface of the patient's nose.

20. The patient interface of claim 1, wherein the two protrusions are configured to only engage respective inner peripheral edges of the patient's nares, in use.

21. The patient interface of claim 1, wherein the two protrusions are configured so that they are only long enough to engage respective inner peripheral edges of the patient's nares, in use.

22. The patient interface of claim 1, wherein the plenum base and the cradle base are formed from the same material.

23. The patient interface of claim 22, wherein the plenum base and the cradle base are formed from a single homogeneous piece of material.

24. The patient interface of claim 1, wherein the cradle base and the plenum base have the same flexibility.

25. A patient interface configured to deliver a pressurized flow of respiratory gas to a patient's airways, the patient interface comprising:
- a plenum base, at least a portion of an outer surface of the plenum base being flexible;
- a cradle base with a pair of lateral portions on opposite lateral sides of the cradle base, the cradle base being configured to engage and form a seal with the patient's nose in use, the plenum base and the cradle base together forming a plenum chamber;
- a flexible interface between the cradle base and the plenum base that is configured to decouple movement between the cradle base and the plenum base, the flexible interface comprising a channel in an outer surface of the plenum base adjacent to the cradle base; and
- a pair of projections extending from the cradle base, the pair of projections being configured to be inserted into the patient's nares in use,
- wherein the pair of projections form a gas flow path from the plenum chamber to the patient's airways in use,
- wherein the lateral portions of the cradle base are configured so that there is a gap between the plenum base and at least part of the lateral portions of the cradle base, and
- wherein the plenum base and the cradle base are inflatable to force a sealing surface of the cradle base against the patient's nose in use.

26. The patient interface of claim 25, wherein the channel forms a complete loop around the cradle base.

27. The patient interface of claim 25, wherein the cradle base is U-shaped or V-shaped.

28. The patient interface of claim 25, wherein the lateral portions of the cradle base are configured to flex toward and away from the plenum base.

29. The patient interface of claim 25, wherein each of the projections extends from a respective one of the lateral portions of the cradle base.

30. The patient interface of claim 29, wherein the lateral portions of the cradle base extend laterally beyond the projections.

31. The patient interface of claim 25, wherein the plenum base comprises a pair of gas inlets, each gas inlet being located at a respective lateral side of the plenum base.

32. The patient interface of claim 25, wherein each projection is configured to seal inside of the patient's nares.

33. The patient interface of claim 25, wherein the cradle base is configured to seal against an outside surface of patient's nares.

34. A patient interface configured to deliver a pressurized flow of respiratory gas to a patient's airways, the patient interface comprising:
- a plenum base pressurisable to a therapeutic pressure of at least 6 cmH$_2$O above ambient air pressure, said plenum base including a plenum chamber inlet port sized and structured to receive a flow of air at the therapeutic pressure for breathing by the patient;
- a seal-forming structure comprising a cradle base and two protrusions extending from the cradle base, each of the protrusions having formed therein an opening configured to allow a continuous flow of air therethrough, each of the protrusions being structured and arranged to be inserted into, or partly into, a respective one of the patient's nares in use to provide the flow of air at said therapeutic pressure to the patient's nares, each of the cradle base and the two protrusions being constructed and arranged to form a seal with a region of the patient's face surrounding and inside the patient's nostrils, the seal-forming structure constructed and arranged to maintain said therapeutic pressure in the plenum base throughout the patient's respiratory cycle in use; and
- a flexible interface between the seal-forming structure and the plenum base, the flexible interface comprising a spring or damper, the spring or damper being configured to decouple movement of the seal-forming structure from the plenum base,
- wherein the cradle base comprises lateral portions that extend laterally outward beyond the flexible interface so that there is a gap between the plenum base and at least part of the lateral portions of the cradle base, and
- wherein the plenum base and the cradle base are inflatable to force a sealing surface of the cradle base against the patient's nose in use.

35. The patient interface according to claim 34, wherein the protrusions are configured to form a seal with the inside of the patient's nares.

36. The patient interface according to claim 34, wherein the cradle base is configured to cradle the patient's nose and form a seal with a surface outside of the patient's nares, in use.

37. The patient interface according to claim 34, wherein only a central portion of cradle base is attached to plenum base.

38. The patient interface according to claim 34, wherein the lateral portions of the cradle base are flexible toward and away from plenum base.

39. The patient interface according to claim 34, wherein the protrusions are angled relative to a surface of the cradle base from which the protrusions extend.

40. A patient interface configured to deliver a pressurized flow of respiratory gas to a patient's airways, the patient interface comprising:
- a plenum base pressurisable to a therapeutic pressure of at least 6 cmH2O above ambient air pressure, said plenum base including an inlet port sized and structured to receive a flow of air at the therapeutic pressure for breathing by the patient; and
- a seal-forming structure constructed and arranged to form a seal with a region of the patient's face surrounding and inside the patient's nostrils, the seal-forming structure being constructed and arranged to maintain said therapeutic pressure in the plenum base throughout the patient's respiratory cycle in use,
- wherein the seal-forming structure comprises a cradle base and a pair of protrusions extending from the cradle base, the cradle base being configured to form a seal with the patient's nose, each protrusion having formed therein an opening configured to convey the flow of air at said therapeutic pressure to the patient's nares in use, each protrusion being configured to be inserted into, or partly into, one of the patient's nares in use, wherein the cradle base is supported on the plenum base by way of a flexible interface comprising one or more folds configured to decouple movement of the cradle base from the plenum base, wherein the cradle base comprises lateral portions that extend laterally outward beyond the flexible interface so that there is a gap between the plenum base and at least part of the lateral portions of the cradle base, wherein the plenum base and the cradle base are inflatable to force a sealing surface of the cradle base against the patient's nose in use.

41. The patient interface of claim 40, wherein the one or more folds is part of a concertina structure.

42. The patient interface of claim 40, wherein the lateral portions extend laterally beyond the protrusions, the lateral portions being configured to seal respectively against a lateral or inferior part of each of the patient's nasal ala in use.

43. The patient interface of claim 40, wherein the patient interface further comprises a positioning and stabilising structure to provide a force to hold the seal-forming structure in a therapeutically effective position on the patient's head.

44. The patient interface of claim 43, wherein the positioning and stabilising structure comprises a tie, the tie being constructed and arranged so that at least a portion overlies a region of the patient's head superior to an otobasion superior of the patient's head in use.

45. The patient interface of claim 43, wherein the positioning and stabilising structure comprises at least one gas delivery tube constructed and arranged to contact at least a region of the patient's head superior to an otobasion superior of the patient's head in use, wherein a portion of the gas delivery tube superior to the otobasion superior of the patient's head comprises, or is provided to, a connection port configured to receive the flow of air from an air circuit and to deliver the flow of air to the entrance of the patient's airways via the seal-forming structure.

* * * * *